(12) United States Patent
　　Mulcahey

(10) Patent No.: US 12,564,434 B2
(45) Date of Patent: Mar. 3, 2026

(54) DEVICES AND METHODS FOR FLUID DISTRIBUTION FROM A CATHETER

(71) Applicant: UNITED STATES ENDOSCOPY GROUP, INC., Mentor, OH (US)

(72) Inventor: Thomas I. Mulcahey, Bedford, MA (US)

(73) Assignee: UNITED STATES ENDOSCOPY GROUP, INC., Mentor, OH (US)

( * ) Notice: Subject to any disclaimer, the term of this patent is extended or adjusted under 35 U.S.C. 154(b) by 1130 days.

(21) Appl. No.: 17/536,911

(22) Filed: Nov. 29, 2021

(65) Prior Publication Data

US 2022/0079649 A1　　Mar. 17, 2022

Related U.S. Application Data

(63) Continuation of application No. 16/280,976, filed on Feb. 20, 2019, now Pat. No. 11,185,360.

(Continued)

(51) Int. Cl.
　　*A61M 25/00*　　　　(2006.01)
　　*A61B 18/02*　　　　(2006.01)
　　　　　　　　(Continued)

(52) U.S. Cl.
　　CPC ..... *A61B 18/0218* (2013.01); *A61M 25/0045* (2013.01); *A61M 25/0069* (2013.01); *A61M 25/0074* (2013.01); *A61B 1/00091* (2013.01); *A61B 2018/00982* (2013.01); *A61B 2018/0212* (2013.01); *A61B 2018/0262* (2013.01);
　　　　　　　　(Continued)

(58) Field of Classification Search
　　CPC .......... A61B 18/00; A61B 2018/00571; A61B 2018/00577; A61B 18/02; A61B 2018/0231; A61B 18/0218; A61B 1/00091; A61B 2018/00982; A61B 2018/0212; A61B 2018/0262; A61M 2025/0073; A61M 2025/091; A61M 2206/20; A61M 25/0045; A61M 25/0069; A61M 25/007;

(Continued)

(56) References Cited

U.S. PATENT DOCUMENTS 5,328,471　A　　7/1994　Slepian
6,117,386　A　　9/2000　Stiger
(Continued)

FOREIGN PATENT DOCUMENTS

EP　　　　　2254637　A1　　12/2010
WO　　　2002007625　A2　　1/2002
(Continued)

OTHER PUBLICATIONS

Office Action from U.S. Appl. No. 16/280,959 dated Oct. 5, 2023.
(Continued)

*Primary Examiner* — Jason E Flick
(74) *Attorney, Agent, or Firm* — Calfee, Halter & Griswold LLP

(57) ABSTRACT

The present disclosure relates generally to the field of medical devices. In particular, the present disclosure relates to devices and methods to convey fluid delivered from a delivery catheter. Exemplary catheters are disclosed which include fluid distribution devices for delivery of fluid and delivery of pass-through medical instruments, such as cryo-decompression tubes, within body lumens.

6 Claims, 16 Drawing Sheets

Related U.S. Application Data

(60) Provisional application No. 62/633,121, filed on Feb. 21, 2018.

(51) Int. Cl.

| | | |
|---|---|---|
| *A61B 1/00* | (2006.01) | |
| *A61B 18/00* | (2006.01) | |
| *A61M 25/06* | (2006.01) | |
| *A61M 25/09* | (2006.01) | |

(52) U.S. Cl.
CPC ... *A61M 25/007* (2013.01); *A61M 2025/0073* (2013.01); *A61M 25/0662* (2013.01); *A61M 2025/091* (2013.01); *A61M 2206/20* (2013.01)

(58) Field of Classification Search
CPC .......... A61M 25/0074; A61M 25/0662; A61M 25/00; A61M 25/0067; A61M 25/0068
See application file for complete search history.

(56) References Cited

U.S. PATENT DOCUMENTS

| | | | |
|---|---|---|---|
| 6,179,816 B1 | 1/2001 | Mottola et al. | |
| 6,540,722 B1 | 4/2003 | Boyle et al. | |
| 6,875,193 B1 | 4/2005 | Bonnette et al. | |
| 6,969,373 B2 | 11/2005 | Schwartz et al. | |
| 7,217,255 B2 | 5/2007 | Boyle et al. | |
| 8,469,919 B2 | 6/2013 | Ingle et al. | |
| 2008/0281317 A1 | 11/2008 | Gobel | |
| 2009/0235325 A1 | 9/2009 | Rozenberg et al. | |
| 2010/0276505 A1* | 11/2010 | Smith ................. | B23K 26/384 |
| | | | 408/19 |
| 2013/0110100 A1 | 5/2013 | Groves | |
| 2015/0272669 A1 | 10/2015 | Brucker et al. | |
| 2017/0172603 A1* | 6/2017 | Bonnette ............. | A61M 25/007 |
| 2018/0008802 A1 | 1/2018 | Ganapathy | |
| 2018/0140302 A1 | 5/2018 | Pai et al. | |
| 2018/0207399 A1 | 7/2018 | Chou | |
| 2018/0271354 A1* | 9/2018 | Tilson ................ | A61B 1/00148 |
| 2019/0209312 A1 | 7/2019 | Zhang | |

FOREIGN PATENT DOCUMENTS

| | | | |
|---|---|---|---|
| WO | 2011/019030 | | 2/2011 |
| WO | 2011091533 | A1 | 8/2011 |
| WO | 2013032846 | A1 | 5/2013 |
| WO | 2016062215 | A1 | 4/2016 |
| WO | 2017041052 | A1 | 3/2017 |

OTHER PUBLICATIONS

Response to Office Action from U.S. Appl. No. 16/280,959 dated Jan. 4, 2024.

Author unknown, "Cryogenic liquid microjet generation" Grisenti Research Group [online] date unknown [retrieved on Aug. 16, 2019]. Retrieved from Internet URL:https:t/www.atom.uni-frankfurt.de/hhng-grisenti/cryogenic__,liquid ___ mircojet ___ generation.html, 3 pages.

International Search Report and Written Opinion for International application No. PCT/US2019/018829, mailed on May 23, 2019, 10 pages.

International Search Report and Written Opinion for International application No. PCT/US2019/018832, mailed on May 25, 2019, 10 pages.

Office Action from U.S. Appl. No. 16/280,976 dated Feb. 3, 2021.

Amendment from U.S. Appl. No. 16/280,976 dated Jul. 1, 2021.

Notice of Allowance from U.S. Appl. No. 16/280,976 dated Jul. 28, 2021.

Restriction Requirement from U.S. Appl. No. 16/280,959 dated Feb. 17, 2022.

Response to Restriction Requirement from U.S. Appl. No. 16/280,959 dated May 17, 2022.

Office Action from U.S. Appl. No. 16/280,959 dated Jun. 8, 2022.

Response to Office Action from U.S. Appl. No. 16/280,959 dated Apr. 19, 2023.

* cited by examiner

SEE FIG. 7D

SEE FIG. 7C

SEE FIG. 7B

722

720

720p

734

732

726

752

DEVICES AND METHODS FOR FLUID DISTRIBUTION FROM A CATHETER

PRIORITY

This application is a continuation of U.S. patent application Ser. No. 16/280,976, filed Feb. 20, 2019, which claims the benefit of priority under 35 USC § 119 to U.S. Provisional Patent Application Ser. No. 62/633,121, filed Feb. 21, 2018, which is incorporated by reference herein in its entirety and for all purposes.

FIELD

The present disclosure relates generally to the field of medical devices. In particular, the present disclosure relates to devices and methods to convey fluid delivered from a delivery catheter. Exemplary catheters are disclosed which include fluid distribution devices for delivery of fluid and delivery of pass-through medical instruments, such as cryo-decompression tubes, within body lumens.

BACKGROUND

Various catheters are used within body lumens for various applications, including to deliver fluids, as a diagnostic or treatment option, to a body lumen. The fluid may be a liquid, a gas, or a mixture of both a liquid and a gas. The delivery may involve spraying the fluid on a wall of the body lumen. In some cases, the efficacy and/or efficiency of the procedure may be dependent on how unobstructed the delivered fluid is to the wall of the body lumen from the catheter and/or spray device.

As an example, cryosurgery is a procedure in which diseased, damaged or otherwise undesirable tissue (collectively referred to herein as "target tissue") is treated by delivery of a cryogen under pressure, which may be a cryogen spray. These systems are typically referred to as cryoablation systems, cryospray systems, cryospray ablation systems, cryosurgery systems, cryosurgery spray systems and/or cryogen spray ablation systems. As typically used, "cryogen" refers to any fluid (e.g., gas, liquefied gas or other fluid known to one of ordinary skill in the art) with a sufficiently low boiling point (i.e., below approximately −153° C.) for therapeutically effective use during a cryogenic surgical procedure. Suitable cryogens may include, for example, argon, nitrogen and helium. Pseudo-cryogens such as carbon dioxide and nitrous oxide that have a boiling temperature above −153° C., but still very low when compared to atmospheric and bodily temperatures (e.g., −88.5° C. for $N_2O$, −78.5° C. for $CO_2$), may also be used.

During operation of a cryospray system, a medical professional (e.g., clinician, technician, medical professional, surgeon and the like) may direct a cryogen spray onto the surface of a treatment area via a cryogen delivery catheter. The medical professional may target the cryogen spray visually through a video-assisted device or endoscope, such as a bronchoscope, gastroscope, colonoscope, ureteroscope, or pediatric scope. Cryogen spray may exit the cryogen delivery catheter at a temperature ranging from 0° C. to −196° C., causing the target tissue to freeze.

Procedures in the body at treatment sites may include catheters along with other instruments necessary to the procedures, in various forms, for different applications, and across a range of treatment sites. For example, during spray cryotherapy, a cryodecompression tube (CDT), gas removal tube (GRT), or gas egress tube (GET) must be placed into the stomach before treating the esophagus in order to evacuate cryogen gas that is generated during the treatment. The tube typically may lay remote to the treatment device against the surface of the body lumen, which may create an untreated area behind the tube, with respect to the spray device (i.e., the tube may block the cryogen spray from reaching the tissue at the treatment site). During therapy, if the tube masks the cryospray, the adjacent tissue may be prevented from fully freezing. The clinician must remove and reorient the tube and/or cryogen delivery device/catheter in a different position to treat the untreated area or return for a second procedure. Such tubes or other instruments may be placed over a guidewire; however, guidewires present an additional potential obstruction in the working channel of the endoscope or at the treatment site, or both.

It is with respect to these considerations that the devices, systems and methods of the present disclosure may be useful.

SUMMARY

The present disclosure in its various embodiments includes devices, systems and methods for distribution of fluids, such as cryospray, and may be used to more efficiently deliver and distribute fluids to treatment areas in tandem with other medical instruments. Such devices and methods may provide, among other benefits, a more efficient coverage of treatment fluid, such as cryospray, at treatment sites. Various embodiments allow instruments to extend through a lumen of a device that also has a cavity portion for fluid delivery, allowing for fluids and/or spray to be uninhibited by instruments at the treatment site.

In various embodiments, a device may include a body having a proximal end, a distal end, and a wall having a width extending therebetween along a longitudinal axis of the body. The body may define a cavity portion and an instrument lumen. An inlet may be at the proximal end of the body. The inlet may extend into and may be in fluid communication with the cavity portion. The inlet may be configured to accept a distal end of a delivery catheter. The instrument lumen may extend through the body and may be parallel to the longitudinal axis from an opening at the proximal end of the body to an opening at the distal end of the body. The instrument lumen may be configured to receive an instrument extending therethrough. One or more apertures may be along the wall of the body in fluid communication with the cavity portion, so that a fluid delivered from the catheter may flow into the cavity portion through the inlet and out of the cavity portion through the one or more apertures.

In various embodiments described here and otherwise, the inlet may include an elongate surface extending at least partially into the cavity portion. The elongate surface may include a step-down portion within the cavity portion. The step-down portion may have a diameter that is smaller than a diameter of the remainder of the elongate surface. The one or more apertures may include spray apertures. The cavity portion may be an annulus. The cavity portion may extend about and may be closed to the instrument lumen. The cavity portion may be open to the inlet so as to convey a fluid delivered from the delivery catheter into the cavity portion through the inlet and out of the cavity portion through the one or more apertures. The body may have a pear-shaped cross-section. The inlet may be parallel to the instrument lumen. The catheter may be removably attachable to the body. The catheter may be permanently attached to the body. The instrument lumen may be substantially perpendicular to the one or more apertures. The body may have a blunt tip at the distal end. A plurality of flow channels may be within the cavity portion. The flow channels may be configured to distribute flow from the inlet, through the cavity portion, and out the one or more apertures. The one or more apertures may include a straight lumen extending through the wall of the body. The one or more apertures may include a frusto-conical shape spanning the width of the wall of the body. A diameter of the apertures that may be on an interior surface of the wall may be larger than a diameter of the apertures that may be on an exterior surface of the wall. The one or more apertures may span a width of the wall at an angle perpendicular to the wall. The one or more apertures may span a width of the wall at an angle to the wall. The angle may be about 15 degrees to about 165 degrees. Some of the one or more apertures may span the width of the wall at an angle that is not perpendicular to the wall. Some of the other one or more apertures may span the width of the wall at an angle perpendicular to the wall. The one or more apertures may create a spray pattern of fluid delivered therefrom about a full circumference of the body.

In various of the embodiments, a system may include a delivery catheter that may have a proximal end, a distal end, and a delivery lumen therebetween. A fluid distribution device may be coupled to the distal end of the catheter. The fluid distribution device may include a body that may have a proximal end, a distal end, and a wall having a width extending therebetween along a longitudinal axis of the body. An inlet may be at the proximal end of the body. The inlet may be configured to couple to the distal end of the delivery catheter. A plurality of raised elements may be disposed on the wall. Portions of the raised elements may extend radially outward from the longitudinal axis. A plurality of channel apertures may each be disposed on the wall between adjacent raised elements of the plurality of raised elements. A plurality of channels may be in fluid communication with the inlet and may each extend to a respective one or more of the plurality of channel apertures. An instrument lumen may extend through the body substantially parallel to the longitudinal axis from a proximal opening at the proximal end of the body to a distal opening at the distal end of the body. The instrument lumen may be configured to accept a medical instrument therethrough. An elongate tubular member may be disposed about the body. A plurality of spray apertures may be disposed about the elongate tubular member. The spray apertures may be disposed between the raised elements. A medical instrument may be disposed through the instrument lumen.

In various of the embodiments described here and otherwise, an expandable member may be included with the system disposed about the body of the fluid distribution device. The expandable member may have a proximal end fixed in position with respect to the delivery catheter. The expandable member may have a distal end fixed in position with respect to the medical instrument. A coating may extend from a distal end of the expandable member and partially toward a proximal end of the expandable member. The coating may be configured to substantially block fluids from advancing distally. An extension tube may be fixed in position with respect to and may extend distally from a distal end of the expandable member. The distal end of the expandable member may be fixed in position by an adhesive, a molded thermoplastic sleeve, cuff, or collar, or by chemical bonding. The adhesive at the distal end of the expandable member may substantially block fluids from advancing distally past the adhesive. The inlet may extend parallel to the instrument lumen. The medical instrument may be one of an endoscope, a guidewire, or a cryodecompression tube, or a combination thereof. A detent may be within the inlet and may be configured to mate with a projection on the catheter to lock the catheter in position with respect to the inlet. The plurality of raised elements may be ribs that extend circumferentially about the longitudinal axis. The body may be permanently attached to the catheter. The spray apertures may be substantially straight lumens through the elongate tubular member. The plurality of spray apertures may include a frusto-conical shape spanning the width of a wall of the elongate tubular member. A diameter of the apertures on an interior surface of the wall may be larger than the diameter on an exterior of the wall. The one or more apertures may span a width of a wall of the elongate tubular member at an angle perpendicular to the longitudinal axis. The one or more apertures may span a width of a wall of the elongate tubular member at an angle to the longitudinal axis. The angle may be about 15 degrees to about 165 degrees. Some of the one or more apertures may span a width of a wall of the elongate tubular member at an angle that is not perpendicular to the longitudinal axis. Other of the one or more apertures may span the width of the wall at an angle perpendicular to the longitudinal axis.

In various embodiments, a device may include a housing that may have a proximal end, a distal end, and extend along a longitudinal axis. An instrument lumen may extend through the housing parallel to the axis from the proximal end to the distal end of the housing. The housing may have a cavity portion defined interior to the housing and extending circumferentially about the instrument lumen. An inlet may extend into the cavity portion from the proximal end of the housing. The inlet may be in fluid communication with the cavity portion and may be configured to accept a distal end of a cryogen fluid delivery catheter. One or more apertures in the housing may be in fluid communication with the cavity portion and may be configured to distribute the cryogen fluid from the catheter and the cavity portion exterior to the housing.

In various of the embodiments described here and otherwise, the one or more apertures may be oriented perpendicular to the longitudinal axis. The inlet may have a diameter configured to interface with the catheter such that the catheter and the inlet may be in substantial contact with each other when coupled together. A plurality of flow channels may be within the cavity portion and may be configured to evenly distribute flow of the cryogen fluid from the catheter from the inlet, through the cavity portion, and out of the one or more apertures. A detent at the inlet may be configured to mate with a projection on the catheter to lock the catheter in position with respect to the inlet.

In various embodiments, a device may include a body having a proximal end, a distal end, and a wall having a width extending therebetween along a longitudinal axis of the body. The body may define a cavity portion. An inlet may extend through the proximal end of the body. The inlet may extend into and may be in fluid communication with the cavity portion. The inlet may be configured to accept a distal end of a delivery catheter. A lumen may extend through the body parallel to the longitudinal axis from an opening at the proximal end of the body to an opening at the distal end of the body. An inner wall may be within the body and may be about the lumen that defines an insulating annulus between the lumen and the cavity portion. One or more apertures may be disposed about and extending through the width of the wall of the body in fluid communication with the cavity portion, so that a fluid delivered from the catheter may flow into the cavity portion through the inlet and out of the cavity portion through the one or more apertures. The insulating annulus may be a substantially sealed vacuum chamber or low-conductivity fill medium suitable for use in the cryogenic temperature range. A transitioning zone may be between and in fluid communication with the inlet and the cavity portion. The transitioning zone may increase in volume in a distal direction. The transitioning zone may include one or more interior walls that may be configured to distribute a flow of the fluid received from the inlet toward the one or more apertures through the cavity portion. The distal end of the lumen may contain an annular barb that may be configured to interface with a tubular member that may extend distally from the lumen and in fluid communication with the lumen. The lumen may extend distally past the body. The body may include a laser cut hypotube. The cavity portion may extend about and may be closed to the instrument lumen. The cavity portion may be open to the inlet so as to convey a fluid delivered from the delivery catheter into the cavity portion through the inlet and out of the cavity portion through the one or more apertures.

In various embodiments, a device may include a body having a proximal end, a distal end, and a wall having a width extending therebetween along a longitudinal axis of the body. An inlet may be at the proximal end of the body. The inlet may be configured to couple to a distal end of a delivery catheter. A plurality of raised elements may be disposed on the wall. Portions of the raised elements may extend radially outward from the longitudinal axis. A plurality of channel apertures may each be disposed on the wall between adjacent raised elements of the plurality of raised elements. A plurality of channels may be in fluid communication with the inlet and may each extend to a respective one or more of the plurality of channel apertures. A lumen may extend through the body substantially in a direction along the longitudinal axis from a proximal opening at the proximal end of the body to a distal opening at the distal end of the body. The lumen may be configured to accept a medical instrument therethrough. An elongate tubular member may be disposed about the body. A plurality of spray apertures may be disposed about the elongate tubular member. The spray apertures may be disposed between the raised elements.

In various of the embodiments described here and otherwise, the plurality of raised elements may be in substantial contact with the elongate tubular member.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

Figure 1:
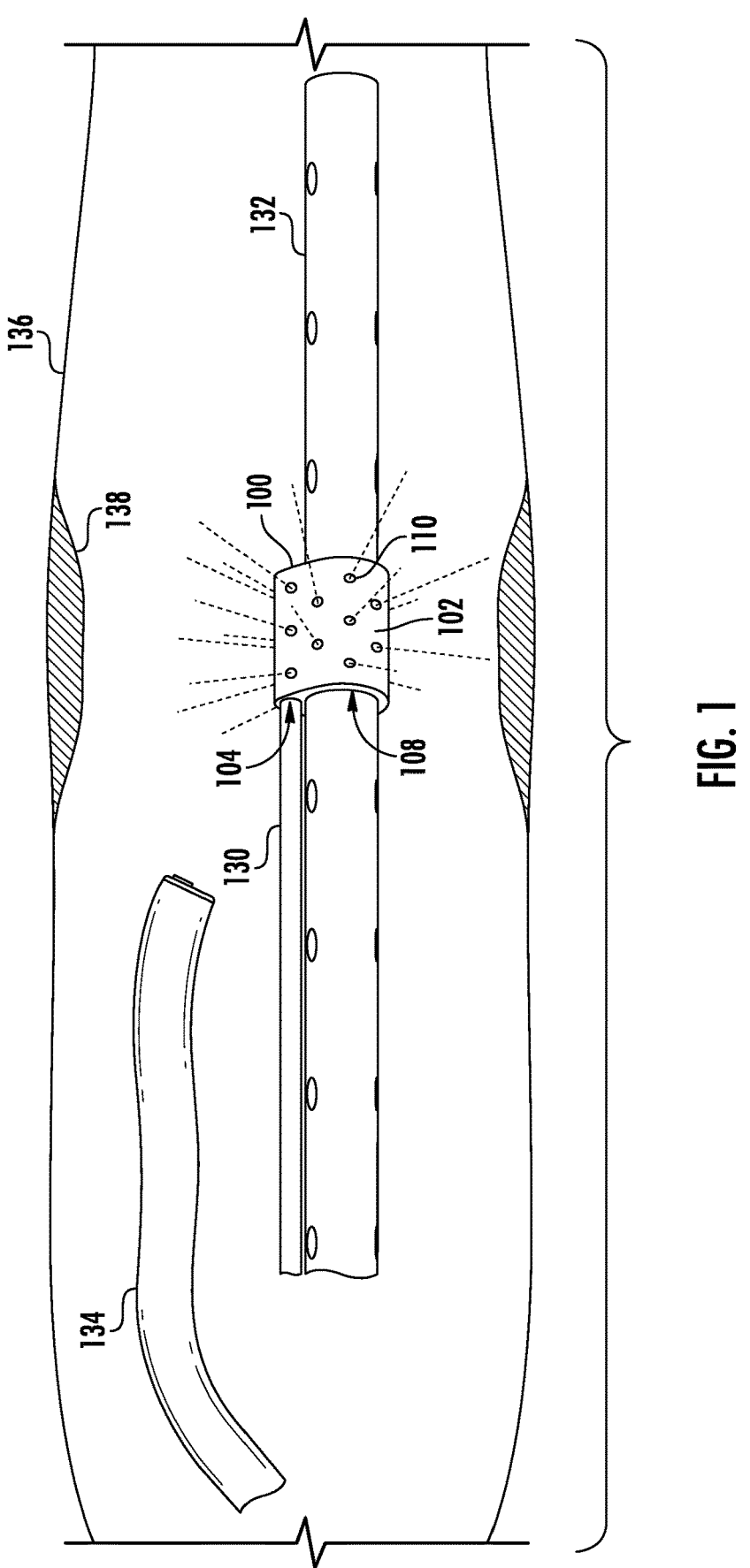
FIG. 1 illustrates a fluid distribution system within a body lumen, in accordance with an embodiment of the present disclosure.

The present disclosure is not limited to the embodiments described. The terminology used herein is only for the purpose of describing particular embodiments and is not intended to be limiting. Unless otherwise defined, all technical terms used herein have the same meaning as commonly understood by one of ordinary skill in the art to which the disclosure belongs.

Although embodiments of the present disclosure may be described with specific reference to cryogen fluid distribution from a catheter within the esophagus or bronchi and with a cryodecompression tube (CDT), it should be appreciated that such devices, systems, and methods may be used with a variety of fluids, with a variety of instruments, and for a variety of other body passageways, organs and/or cavities, such as the vascular system, urogenital system, upper gastrointestinal system, lower gastrointestinal system, and the like.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated portions, regions, steps elements and/or components, but do not preclude the presence or addition of one or more other portions, regions, integers, steps, operations, elements, components and/or groups thereof.

As used herein, the conjunction "and" includes each of the structures, components, portions, or the like, which are so conjoined, unless the context clearly indicates otherwise, and the conjunction "or" includes one or the others of the structures, components, portions, or the like, which are so conjoined, singly and in any combination and number, unless the context clearly indicates otherwise.

As used herein, the term "distal" refers to the end farthest away from the medical professional along a system or device when introducing the system or device into a patient, while the term "proximal" refers to the end closest to the medical professional along the system or device when introducing the system or device into a patient.

The devices and methods of the present disclosure may be used with cryoablation systems to distribute the flow of cryospray gases (hereafter referred to as "cryogen" or "cryospray") within a body lumen. Exemplary cryoablation systems with which the present disclosure may be implemented include, but are not limited to, those systems described commonly owned U.S. Pat. Nos. 9,820,797, 9,301,796, and 9,144,449, and U.S. patent application Ser. Nos. 11/956,890, 14/012,320, and 14/869,814, each of which are herein incorporated by reference in their entirety. In various embodiments, features and advantages of distributing fluid can be realized throughout this disclosure as well as throughout the disclosure of co-owned United States Provisional Patent Application filed concurrently herewith, entitled "Systems and Methods to Enhance Radial Spray from a Catheter" to Downey et al., which is herein incorporated by reference in its entirety and for all purposes.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

Various embodiments of the present disclosure allow for a variety of endoscopic instruments (e.g. a CDT, biopsy devices, stent sizers, stent delivery systems, and the like) to be received and extended through an instrument lumen of a fluid distribution device while a distal end of a delivery catheter is accepted through an inlet of a device. Once the instrument, device, and catheter are advanced to a desirable location in the body lumen, a fluid, such as a cryogen, may be delivered through the catheter, into an inlet of the device, and out of one or more apertures. A fluid sprayed from the one or more apertures may reach a target tissue of a patient without being impeded by the endoscopic instrument extending through the instrument lumen.

With reference to FIG. 1, an embodiment of a fluid distribution system according to the present disclosure is illustrated, which includes a delivery catheter 130 having a proximal end, a distal end, and a lumen therebetween. A fluid distribution device 100 is coupled to the distal end of the catheter 130. The device 100 has a body 102 with a proximal end, a distal end, and a wall having a width extending therebetween along a longitudinal axis of the body 102. The body 102 defines a cavity portion and an instrument lumen 108. The instrument lumen 108 extends through the body 102. The device 100 has an inlet 104 at the proximal end of the body 102. The inlet 104 extends into and is in fluid communication with the cavity portion. The inlet 104 accepts the distal end of the delivery catheter 130. The device 100 includes apertures 110 along the wall of the body 102 in fluid communication with the cavity portion, so that a fluid delivered from the catheter 130 flows into the cavity portion through the inlet 104 and out of the cavity portion through the apertures 110 to distribute a fluid from the catheter 130 and the cavity portion exterior to the body 102. An instrument 132, e.g., a CDT or the like, is received within the instrument lumen 108 and extends therethrough. An endoscope 134, e.g., a pediatric scope or the like, external to the system may be used to observe and position the device 100, catheter 130, and instrument 132. The system is shown inserted into a body lumen 136, and the device 100 is position such that the system may treat a target tissue 138.

Figure 2A:
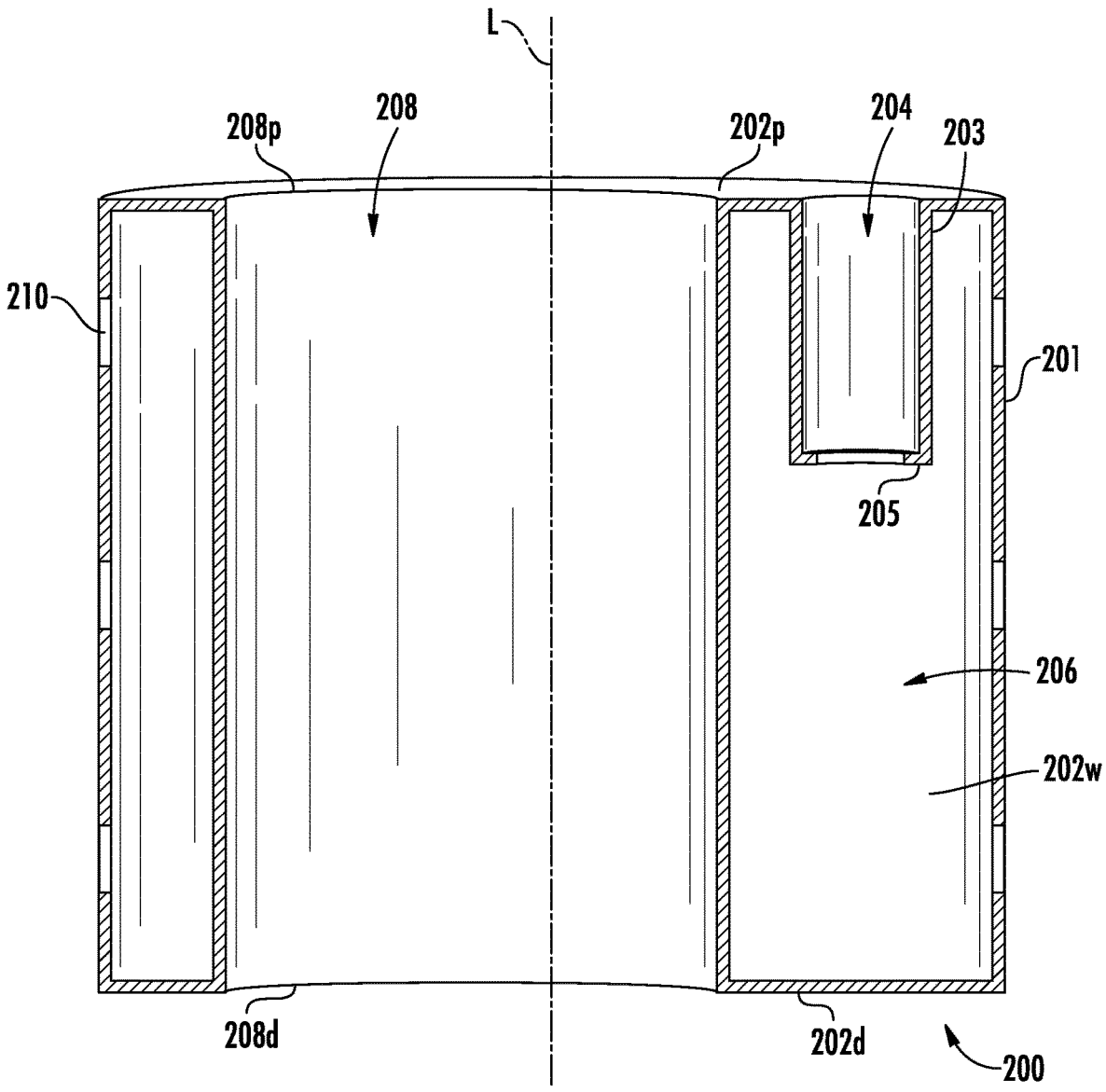
FIG. 2A illustrates a front cross-sectional view of a fluid distribution device in accordance with an embodiment of the present disclosure.
Figure 2B:
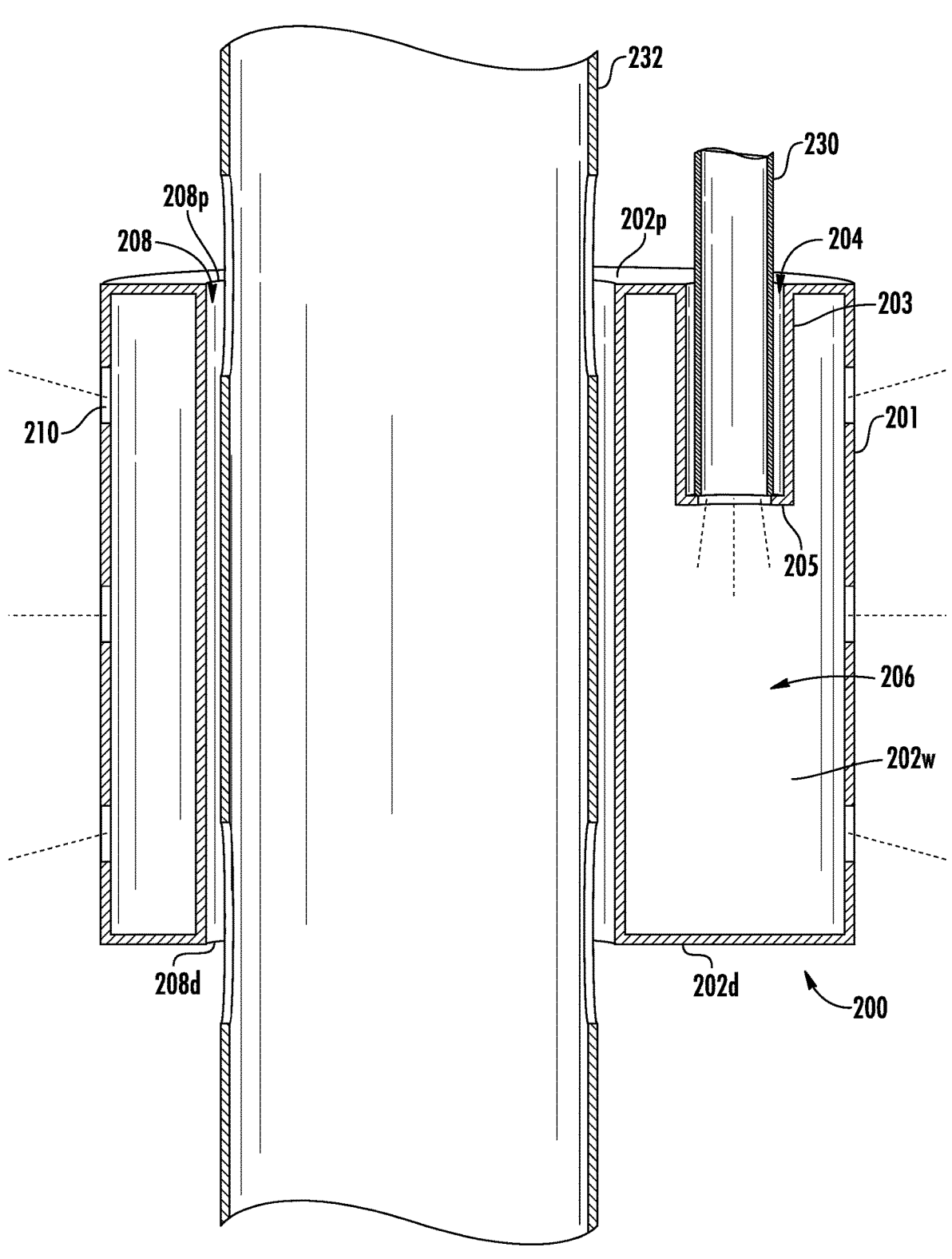
FIG. 2B illustrates a front cross-sectional view of the device of FIG. 2A, as a system with a catheter and an instrument included in accordance with an embodiment of the present disclosure.
Figure 2C:
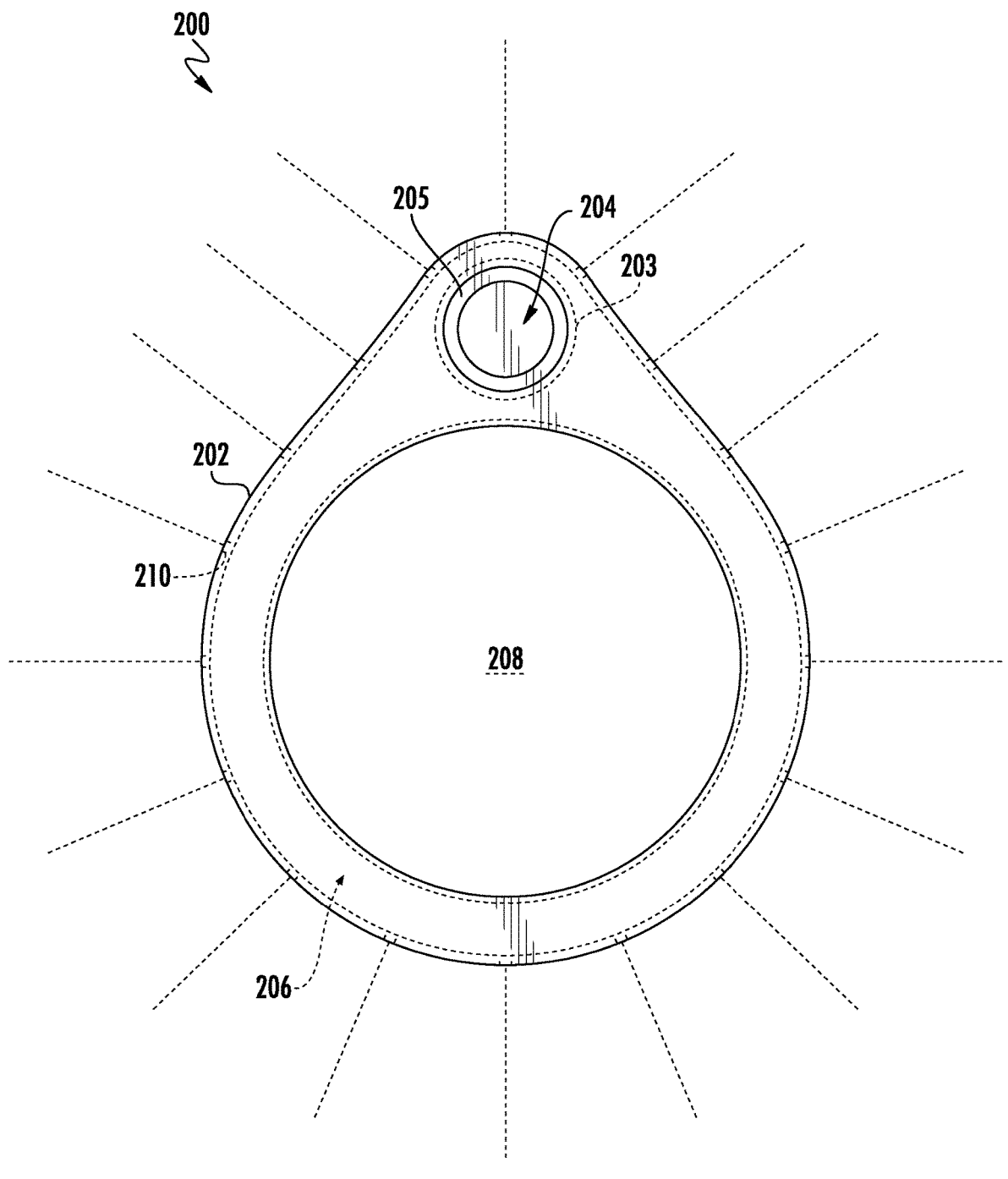
FIG. 2C illustrates a top view of the device of FIGS. 2A and 2B.

With reference to FIGS. 2A through 2C, an embodiment of a fluid distribution device 200 according to the present disclosure is illustrated, which includes a body 202 having a proximal end 202p, a distal end 202d, and a wall 202w having a width extending therebetween extending along a longitudinal axis L of the body 202. The body 202 defines a cavity portion 206 and an instrument lumen 208. There is an inlet 204 through the proximal end 202p of the body. The inlet 204 extends into and is in fluid communication with the cavity portion 206. The inlet 204 is configured to accept a distal end of a delivery catheter 230. The inlet 204 includes an elongate surface 203 that extends at least partially into the cavity portion 206. The elongate surface 203 has a step-down portion 205 within the cavity portion 206, creating a diameter of the opening at the distal end of the inlet that is smaller than a diameter of the remainder of the elongate surface 203 and the diameter of the opening at the proximal end of the inlet. The diameter of the step-down portion 205 is smaller than the outer diameter of the catheter 230. It should be appreciated that the catheter 230 within inlet 204 cannot extend past the step-down portion 205. An instrument lumen 208 extends through the body 202 parallel with the longitudinal axis L from an opening at the proximal end 208p to an opening at the distal end 208d of the body 202. The instrument lumen 208 is configured to receive an instrument 232 extending therethrough. Apertures 210 along the wall 202w of the body 202 are in fluid communication with the cavity portion 206. The cavity portion 206 extends about and is closed to the instrument lumen 208. The cavity portion 206 is open to the distal end of the inlet 204, so as to convey a fluid delivered from the delivery catheter 230 into the cavity 206, through the inlet 204, and out of the cavity portion 206 through the one or more apertures 210, so that the fluid delivered from the catheter 230 flows into the cavity portion 206 through the inlet 204 and out of the cavity portion 206 through the apertures 210 to distribute the fluid from the catheter 230 and the cavity portion 206 exterior to the body 202.

Figure 3:
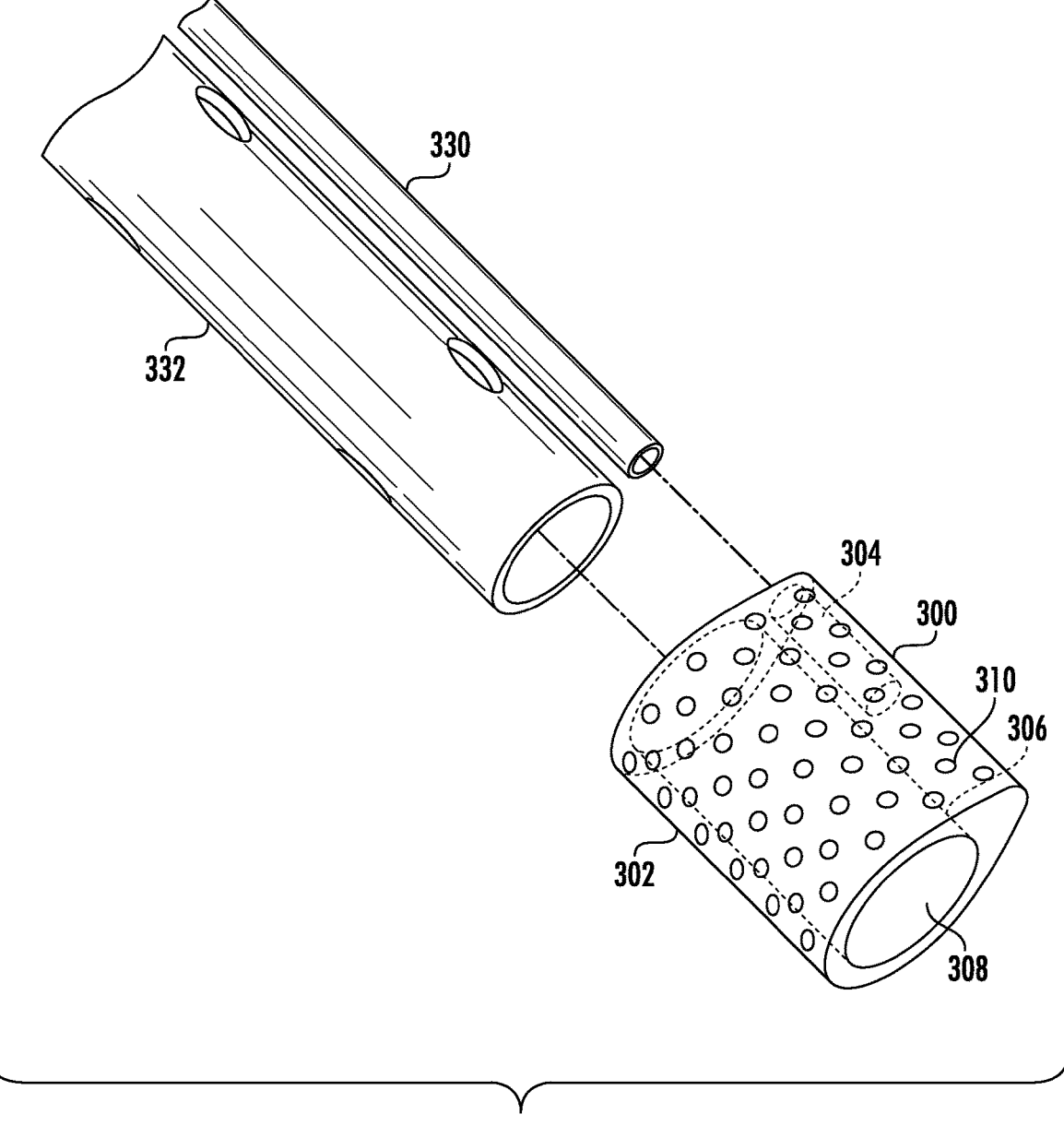
FIG. 3 illustrates a perspective view of a fluid distribution system, in accordance with an embodiment of the present disclosure.

Referring to FIG. 3, an embodiment of a fluid distribution device according to the present disclosure is illustrated, which includes a body 300 having a wall 302 extending along a longitudinal axis of the body 300. An inlet 304 extends through the proximal end of the body 300 and into a cavity portion 306 that is defined by the body 300. The inlet 304 is in fluid communication with the cavity portion 306 and is configured to accept a distal end of a delivery catheter 330. An instrument lumen 308 extends through the body 300 and is configured to receive an instrument 332 extending therethrough. There are apertures 310 along the wall 302 of the body 300 in fluid communication with the cavity portion 306. The cavity portion 306 extends about and is closed to the instrument lumen 308. The cavity portion 306 is open to the distal end of the inlet 304, so as to convey a fluid delivered from the delivery catheter 330 into the cavity portion 306 through the inlet 304 and out of the cavity portion 306 through the apertures 310.

Figure 4A:
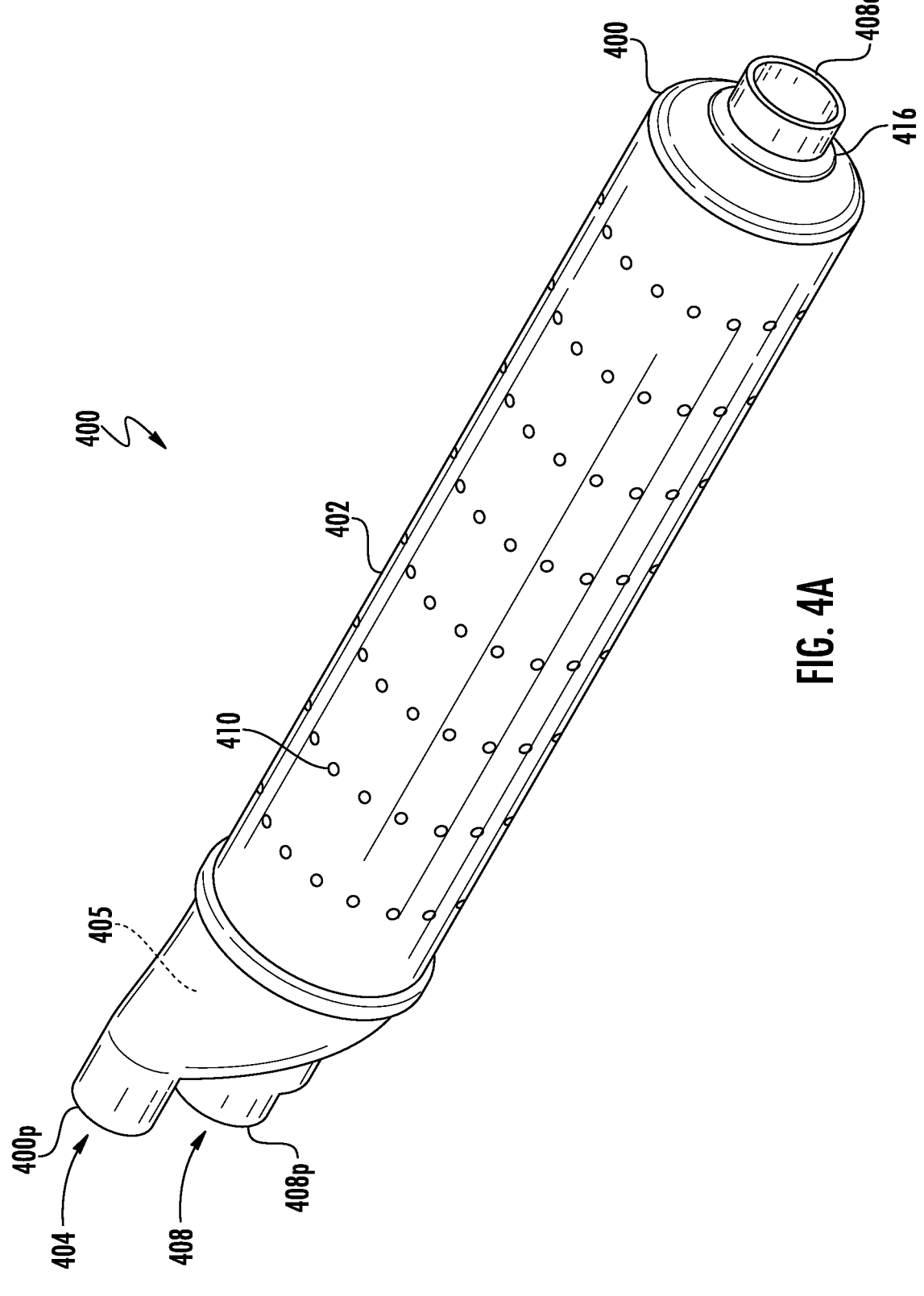
FIGS. 4A and 4B illustrate a perspective and a left cross-sectional view, respectively, of a fluid distribution device, in accordance with an embodiment of the present disclosure.
Figure 4B:
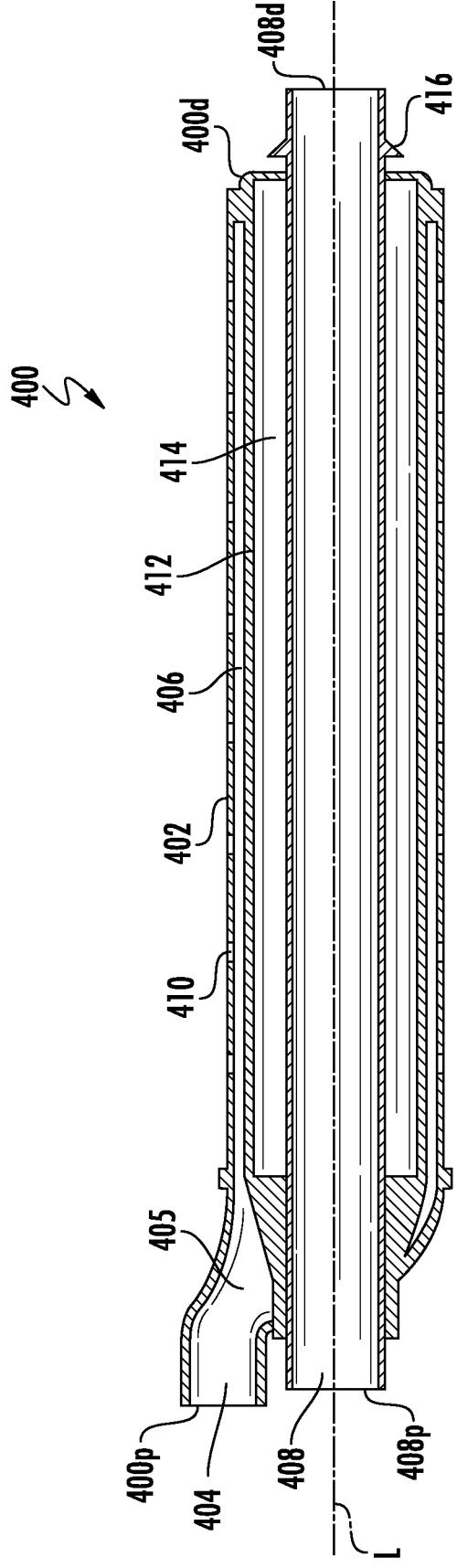

Referring to FIGS. 4A and 4B, an embodiment of a fluid distribution device according to the present disclosure is illustrated, which includes a body 400 having a proximal end 400p, a distal end 400d, and a wall 402 having a width extending along a longitudinal axis L of the body 400. The body 400 defines a cavity portion 406. There is an inlet 404 through the proximal end 400p of the body 400. The inlet 404 extends into and is in fluid communication with the cavity portion 406. A transitioning zone 405 is between and in fluid communication with each of the inlet 404 and the cavity portion 406. The inlet 408 and the cavity portion 406 may each include at least a portion of the transitioning zone 405. The transitioning zone 405 increases in volume in a distal direction (i.e., in a direction substantially toward the distal end of the body 400). The inlet 404 is configured to accept a distal end of a delivery catheter. A lumen 408, which may accept a medical instrument therethrough, extends through the body 400 along the longitudinal axis L from an opening at the proximal end 408p to an opening at the distal end 408d of the body 400. There is an inner wall 412 within the body 400 that is about the lumen 408 that defines an insulating annulus 414 between the lumen 408 and the cavity portion 406. The insulating annulus may substantially insulate the lumen 408 from a fluid within the cavity portion 406. There are apertures 410 disposed about and extending through the width of the wall 402 of the body 400 in fluid communication with the cavity portion 406, so that a fluid delivered from a catheter flows into the cavity portion 406 through the inlet 404 and out of the cavity portion 406 through the one or more apertures 410. The apertures 410 are arranged circumferentially about the wall 402 to allow for circumferential spray coverage of a body lumen. The diameter and distribution of apertures 410 may be varied along and about the axis L to establish desired spray field properties, for example, to achieve substantially uniform flow through all the apertures 410. The cavity portion 406 extends about and is closed to the lumen 408. The cavity portion 406 is open to the distal end of the inlet 404 via the transition zone 405 communicating between the inlet 404 and the cavity portion 406, so as to convey a fluid delivered from the delivery catheter through the inlet 404 into the cavity portion 406 and out of the cavity portion 406 through the apertures 410. The cavity portion 406 may be configured to create uniform flow distribution, for example by tapering the profile of a surface of the inner wall 412 along the axis L, by filling the cavity portion 406 with a porous medium (e.g., packed or sintered powders, textiles, or other engineered fillers (such as pin-fin arrays, guide vane arrays, photochemical etched screens, etc.) known to those familiar with the art), or modifying the wetted surfaces of the cavity portion 406 to promote a substantially uniform phase distribution (e.g., specifying surface roughness to selectively promote or inhibit turbulence, applying hydrophobic or hydrophilic coatings, and combinations thereof).

The distal end 408d includes an annular barb 416 configured to interface with a tubular member that extends distally from the distal end 408d of the lumen 408 and is in fluid communication with the lumen 408. The tubular member may be retained in place by the barb and may extend the lumen 408 distal to the body 400.

Figure 5:
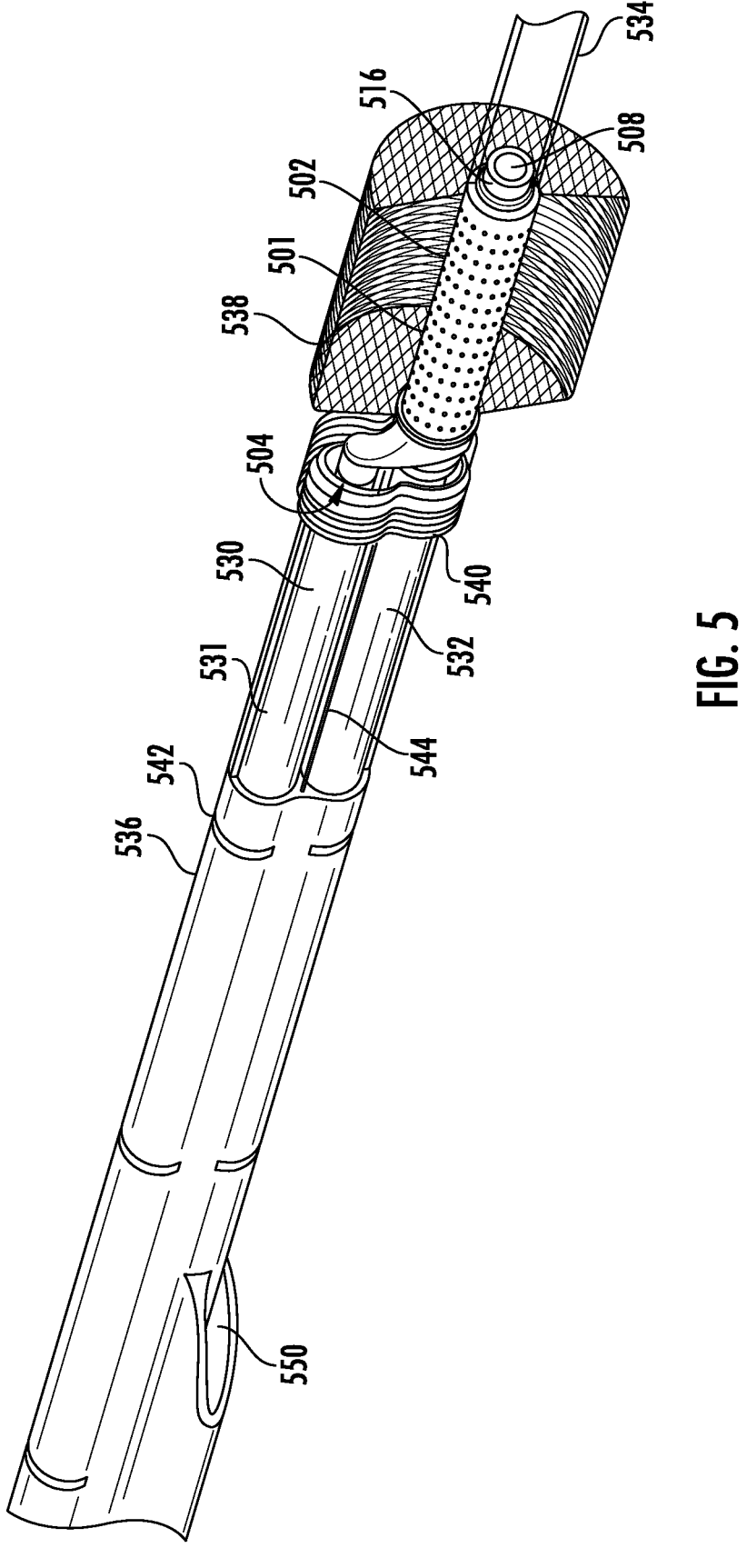
FIG. 5 illustrates a perspective and partial cross-sectional view of a fluid distribution system, in accordance with an embodiment of the present disclosure.

Referring to FIG. 5, an embodiment of a fluid distribution system according to the present disclosure is illustrated, which includes a fluid distribution device 501 coupled to a delivery catheter 530 via an inlet 504 that accepts the catheter 530. A tubular member 534 extends distally from a lumen 508 of a body 502 of the device 501. The tubular member 534 interfaces with an annular barb 516 of a distal end of the lumen 508. The tubular member 534 may be retained in place by the barb and extends the lumen 508 distally. The tubular member 534 may extend distally into a patient, past the target tissue (e.g., into the stomach). A sheath 536 surrounds the catheter 530 with an air or vacuum gap 531 that insulates the catheter 530. The sheath 536 also includes a fluid pathway 532 that is in fluid communication with a proximal end of the lumen 508 and the tubular member 534. The fluid pathway 532 may be configured as an instrument channel to accept the insertion of one or more endoscopic instruments, such as a CDT. For example, an instrument may be inserted into the fluid pathway 532 and through the lumen 508 into the tubular member 534 and out the distal end of tubular member 534. The instrument may be fixed in position with respect to the tubular member 534 or may slidably be translated therethrough. The instrument may have a projection to create friction with a wall of the tubular member. The sheath 536 may be a multi-lumen extrusion. The system includes an expandable member 538 that expands and collapses with the distal and proximal translation of an actuating member 540 at a handle (not shown) at the proximal end of the device 501 via a tether 544 that extends proximally along the sheath 536. Other means of actuation are contemplated. The expandable member 538 is retractable into a collapsed position during insertion, relocation, and removal of the system from the patient. The expandable member 538 may be expanded and made to contact the walls of a body lumen to establish patency, widen the body lumen, unfold or smooth out tissue to be treated, and/or center the instrument within the lumen to be treated. The sheath 536 includes markings 542 that may be used to aid a medical professional in measuring lumens, positioning devices, and tracking treatment within the patient. The sheath 536 also includes a passive venting channel 550 that extends proximally out of the patient, allowing for the passive ventilation of fluids from within the patient in addition to or in place of a CDT (e.g., active or passive ventilation through the fluid pathway 532, and/or through an instrument extending through the fluid pathway 532). An expandable member 538 may have a substantially cylindrical shape that is supported by, e.g., one or more of shape memory elements, a braiding pattern, or a flexible gel or adhesive that may partially solidify throughout a portion of the expandable member 538 to influence its shape.

Figure 6:
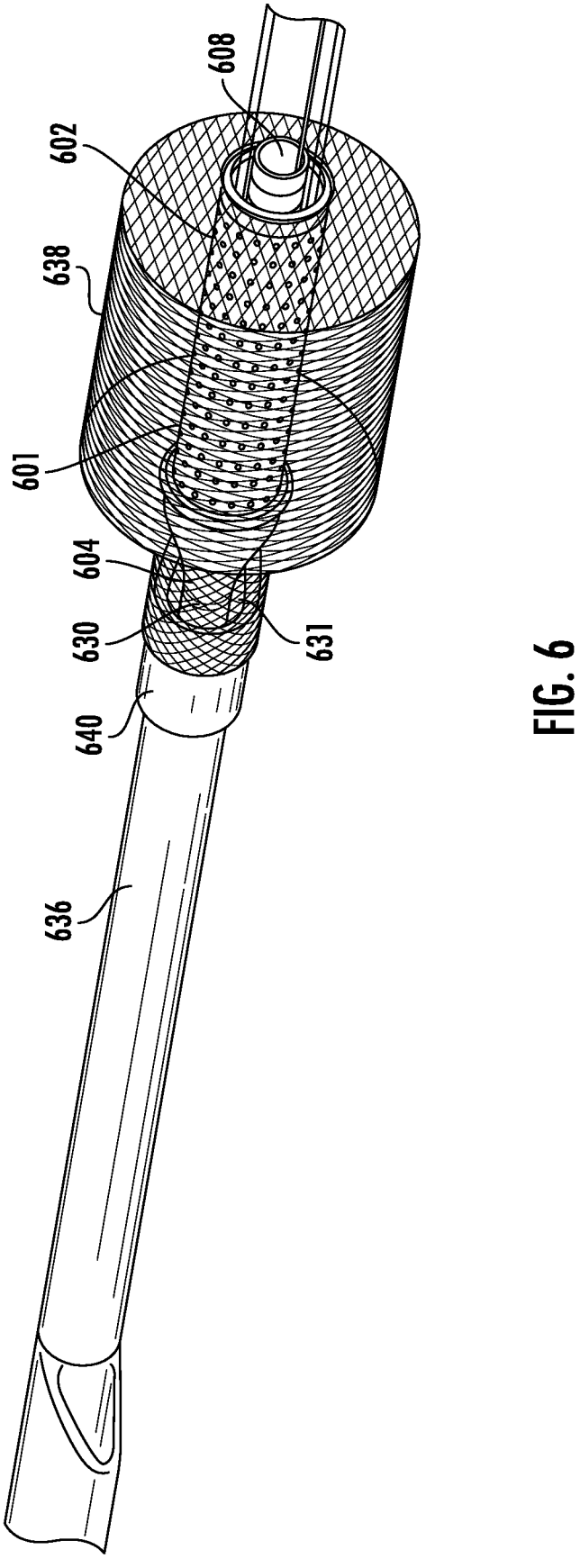
FIG. 6 illustrates a perspective view of a fluid distribution system, in accordance with an embodiment of the present disclosure.

Referring to FIG. 6, an embodiment of a fluid distribution system according to the present disclosure is illustrated, including a fluid distribution device 601 coupled to an annulus channel 630 of a sheath 636 via an inlet 604. The inlet 604 is a substantially annular channel 630 that circumferentially surrounds a lumen 608 extending through the device 601. The annular channel 630 is in fluid communication with the apertures about the device 601 such that a fluid may be supplied from the annular channel 630 and through the apertures. The inlet 604 may transition from a smaller diameter at a proximal end of the inlet 604 (at the annulus channel 630), to a larger diameter in the distal direction and at the distal end of the inlet 604 (at the body 602 of the distribution device 601). The annulus channel 630 extends proximally along the sheath 636 and is in fluid communication with a delivery catheter. An instrument may be in fluid communication with the inlet 604 and/or may extend through the lumen 608. The sheath 636 also includes an air or vacuum gap 631 about the annulus channel 630 that insulates the annulus channel 630, such that the lumen 608 may be substantially insulated from a fluid supplied into the device 601. The lumen 608 is in fluid communication with a fluid pathway that extends proximally along the sheath 636 within the annulus channel 630 but is not in fluid communication with the annulus channel 630. The separation of the lumen 608 from the annulus channel 630 allows for the lumen 608 to maintain a pathway independent of any fluid supplied to the annulus channel 630 (e.g., separating a cryogen fluid pathway from the lumen 608 that may act as a cryodecompression pathway). An expandable member 638 may be disposed about the fluid distribution device 601. The member is shown in an expanded configuration in FIG. 6 and may be expanded and collapsed with the distal and proximal translation of the actuating member 640 about the sheath 636 via a tether that extends proximally along the sheath 636 and out of the patient for actuation by a medical professional. An expandable member 638 may have a substantially cylindrical shape that is supported by, e.g., one or more of shape memory elements, a braiding pattern, or a flexible gel or adhesive that may partially solidify throughout a portion of the expandable member 638 to influence its shape.

Figures 7A, 7B:
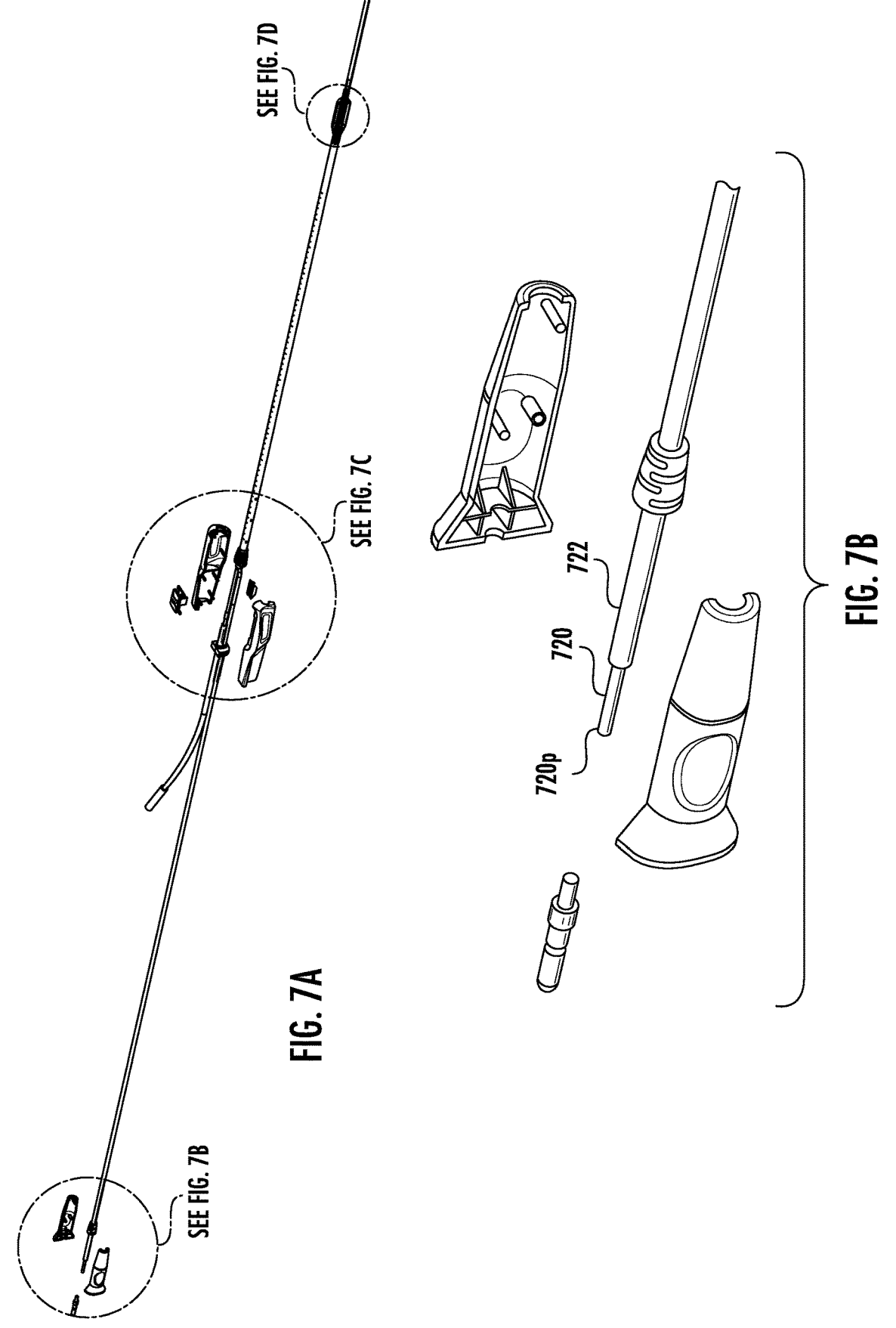
FIGS. 7A-7G illustrate a fluid distribution system, in accordance with an embodiment of the present disclosure.
Figure 7C:
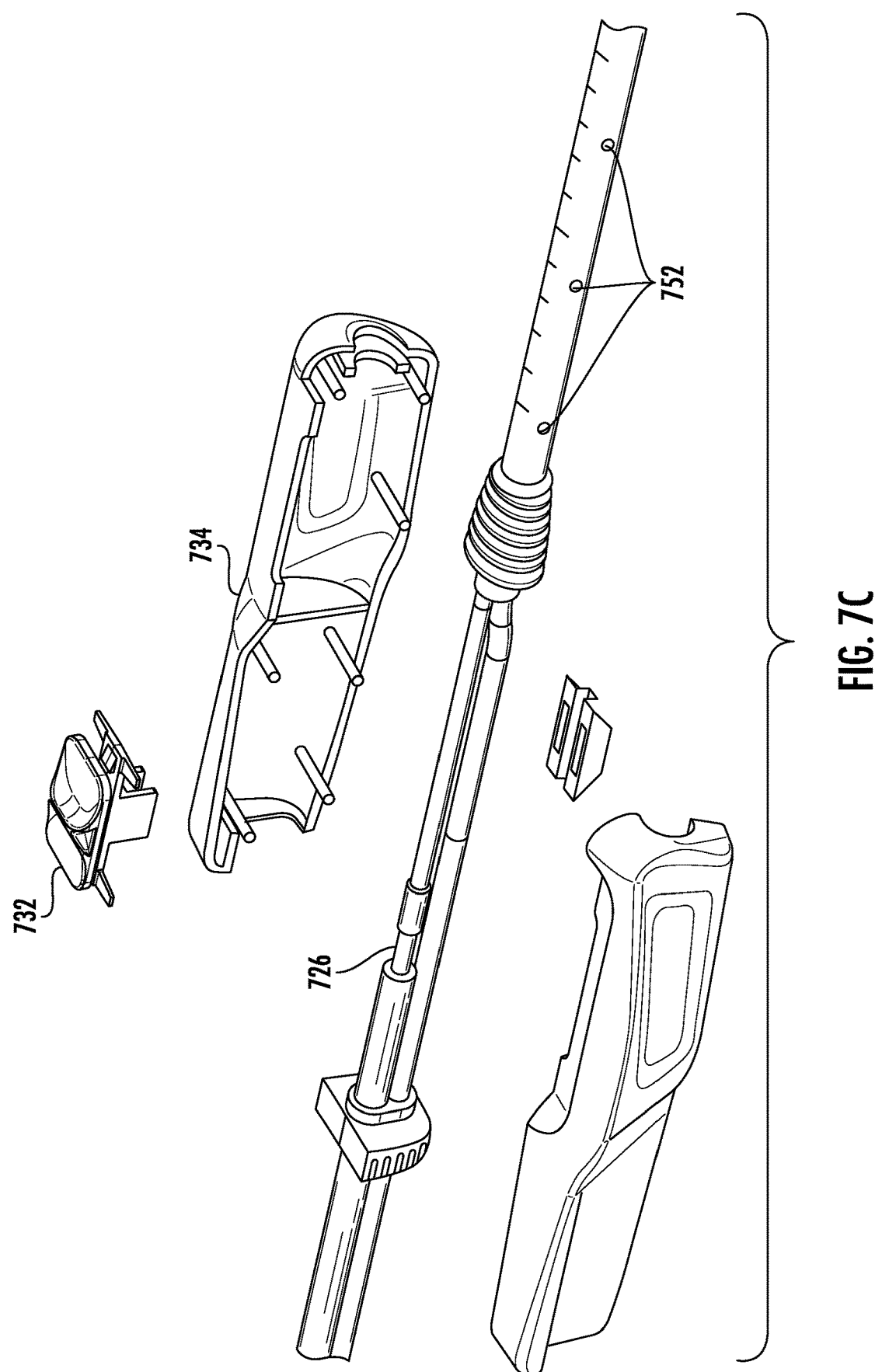
Figure 7D:
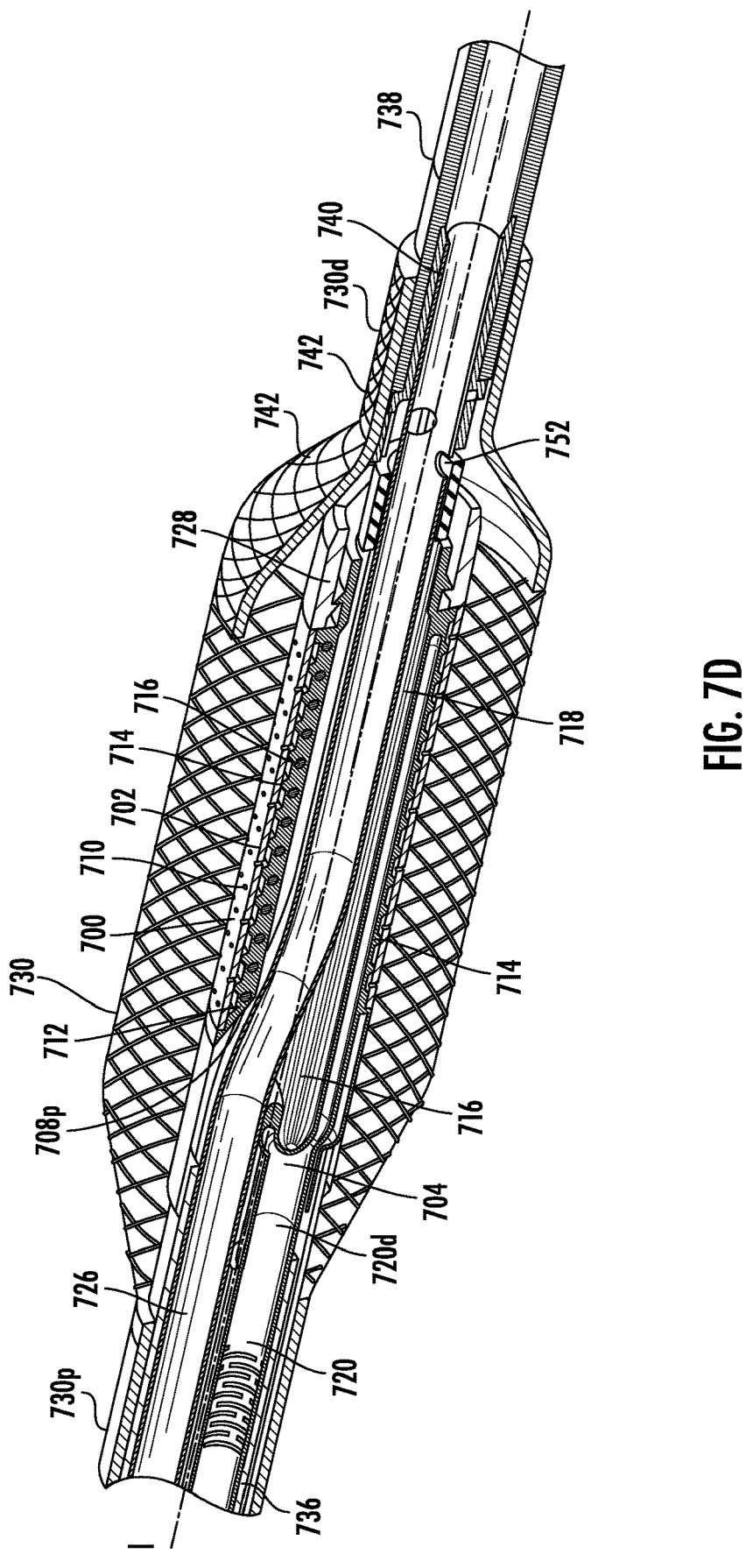
Figures 7E, 7F:
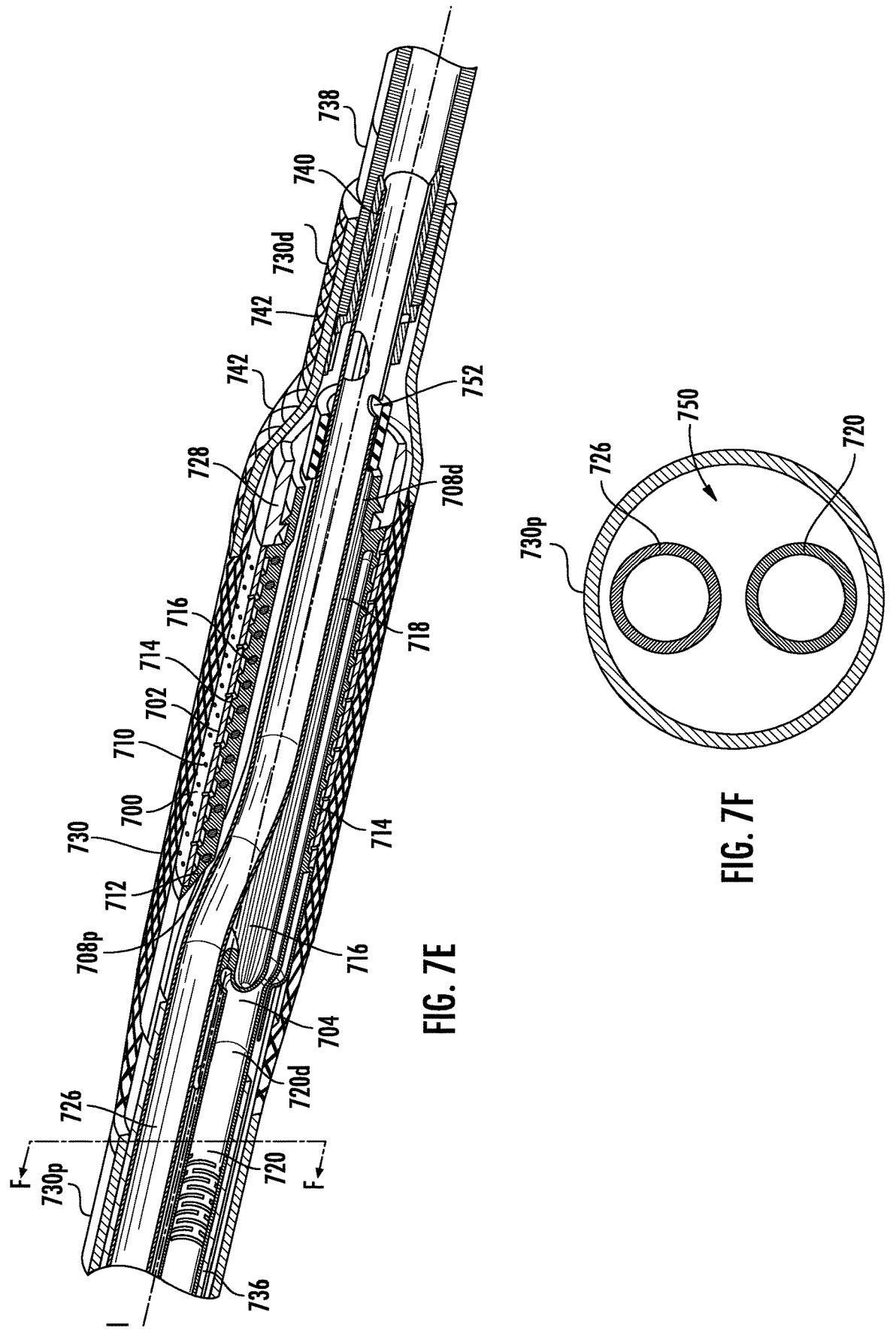
Figure 7G:
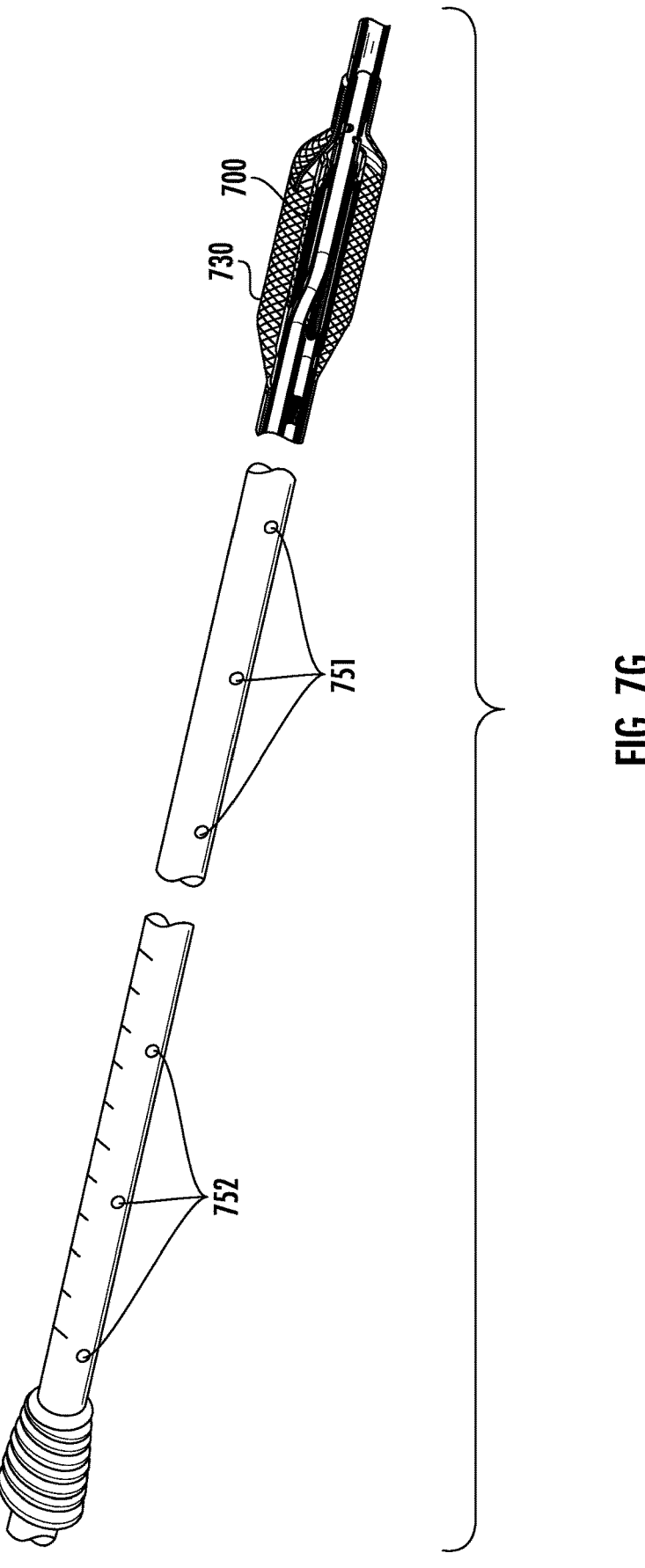

Referring to FIGS. 7A-7G, an embodiment of a fluid distribution system according to the present disclosure is illustrated, which includes a delivery catheter 720 that is enclosed in insulating layers 722 along portions of its length. The delivery catheter 720 has a proximal end 720p, a distal end 720d, and a delivery lumen therebetween. A fluid distribution device 700 is coupled to the distal end 720d of the catheter. The device 700 has a body 712 having a proximal end 712p, a distal end 712d, and a wall 712w having a width extending therebetween along a longitudinal axis L of the body 712. The device 700 has an inlet 704 through the proximal end 712p of the body 712 that is configured to accept the distal end 720d of the delivery catheter 720. There may be raised elements 714 disposed on the wall 712w of the body 712 that extend radially outward from the longitudinal axis L (e.g., ribs). One or more channels 716 in the body 712 extend from the inlet 704 to one or more channel apertures (not shown) in the wall 712w. Each of the one or more channel apertures are situated between adjacent raised elements 714. Each space between adjacent raised elements 714 may have a single channel aperture or multiple apertures. The channels 716 are in fluid communication with the inlet 704 at a proximal end and are in fluid communication with the space between adjacent raised elements 714 at the distal end via the channel apertures. An instrument lumen 708 extends through the body 712 along the longitudinal axis L from a proximal opening 708p at the proximal end of the body 712p to a distal opening 708d at the distal end of the body 712d. A medical instrument 726 extends through the instrument lumen 708. FIG. 7F illustrates a cross-sectional view of the sheath 736 at F-F having a delivery catheter 720, a medical instrument 726, and a passive ventilation lumen 750 about the catheter 720 and the instrument 726. The passive ventilation lumen 750 is in fluid connection with a proximal outlet or outlets

752 so that fluids may passively flow proximally from one or more ventilation inlets 751 through the sheath 736 that may be proximal to the device 700, and out of the system and/or patient through, e.g., ventilation outlet apertures 752 in FIG. 7C.

Still referring to FIGS. 7A-7G, an elongate tubular member 702 having spray apertures 710 surrounds the body 712. The spray apertures 710 are arranged about the circumference of the elongate tubular member 702 in rows such that the spray apertures 710 are disposed between adjacent raised elements 714. However, in various embodiments the apertures 710 and raised elements 714 could be of another arrangement among the channels 716, channel apertures, and spray apertures 710, depending on the desired application and effects. A first cuff 728 is disposed about a distal end 712d of the body 712 that extends the instrument lumen 708 by providing a bearing surface for the medical instrument 726 to slide within and against the first cuff 728 without the medical instrument 726 contacting the instrument lumen 708. The outer profile of cuff 728 may provide a gradually tapering profile for atraumatic intubation. The system includes an expandable member 730 about the fluid distribution device 700. The expandable member 730 is a braided mesh, but may comprise other expandable materials such as, e.g., a compliant or non-compliant balloon, or the like. A proximal end 730p of the expandable member 730 is fixated with respect to the delivery catheter 720 and a distal end 730d of the expandable member 730 is fixated with respect to the medical instrument 726. The attachment points of the expandable member 730 allow for translation of the medical instrument 726 to distally extend and proximally retract the distal end 730d of the expandable member 730 independent of the proximal end 730p. This allows for manipulation of the expandable member 730. For example, the distal end 730d may be moved toward the proximal end 730p such that the expandable member 730 transitions into an expanded configuration as illustrated in FIG. 7D. As another example, the distal end 730d may be moved distally away from the proximal end 730p such that the expandable member 730 transitions into a collapsed configuration as illustrated in FIG. 7E.

Still referring to FIGS. 7A-7G, translation of the medical instrument 726 may be manipulated by using a handle 734 that has a slider 732 coupled to a proximal portion of the medical instrument 726. The proximal and distal ends 730p, 730d of the expandable member 730 may be fixed in position to various portions of the system in order for the proximal end 730p to be fixated with respect to the catheter 720 and the distal end 730d to be fixed in position with respect to the medical instrument 726. The proximal end 730p of the expandable member 730 is fixed to a sheath 736 containing the catheter 720 and the instrument 726, but may instead, e.g., be fixed to the catheter 726 and/or insulation layer(s) 722. The distal end 730d of the expandable member 730 is fixed to an extension tube 738 that extends from the medical instrument 726, but may instead, e.g., be fixed to the medical instrument 726. The medical instrument 726 extends through the first cuff 728 and also a second cuff 740 that is fixed to an inside of a proximal portion of the extension tube 738. The distal end 730d of the expandable member 730 is fixed by a coating 742 that extends from the distal end 730d of the expandable member 730 toward the proximal end 730p of the expandable member 730. The coating 742 forms a barrier membrane that is configured to substantially block fluids from advancing distally past the coating 742 (e.g., cryospray). The coating 742 substantially fills-in gaps in the mesh of the expandable member 730 where it is applied to form a continuous fluid barrier. The coating 742 may be a flexible elastomeric coating to allow for deformation when the expandable member 730 transitions between the expanded configuration and the collapsed configuration. The coating 742 may be applied while the expandable member 730 is in the expanded configuration such that the wall is generally frustum-shaped, funnel-shaped, or the like. The coating 742 may increase the stiffness of the expandable member 730 where the two are in contact such that the shape and radial stability of the expandable member 730 is reinforced by the coating 742. The coating 742 may comprise a variety of materials such as, e.g., a urethane, a molded thermoplastic, thermoplastic urethane, thermosetting urethane, pebax, thermoplastic elastomer, or the like. The second cuff 740 may allow for the insertion and removal of the instrument 726 into the system and/or into a patient independent of insertion or removal of the remaining parts of the system. The second cuff 740 fluidly couples the instrument 726 to the extension tube 738. The second cuff 738 may also adjust the position of the instrument 726, e.g., to position ventilation apertures 752 that may be active or passive to remove fluid from the treatment area and proximally through the instrument 726. Other means of attachment of the components with respect to each other, as described above, are contemplated, such as fasteners, pins, clips, welds, and the like.

Figure 8A:
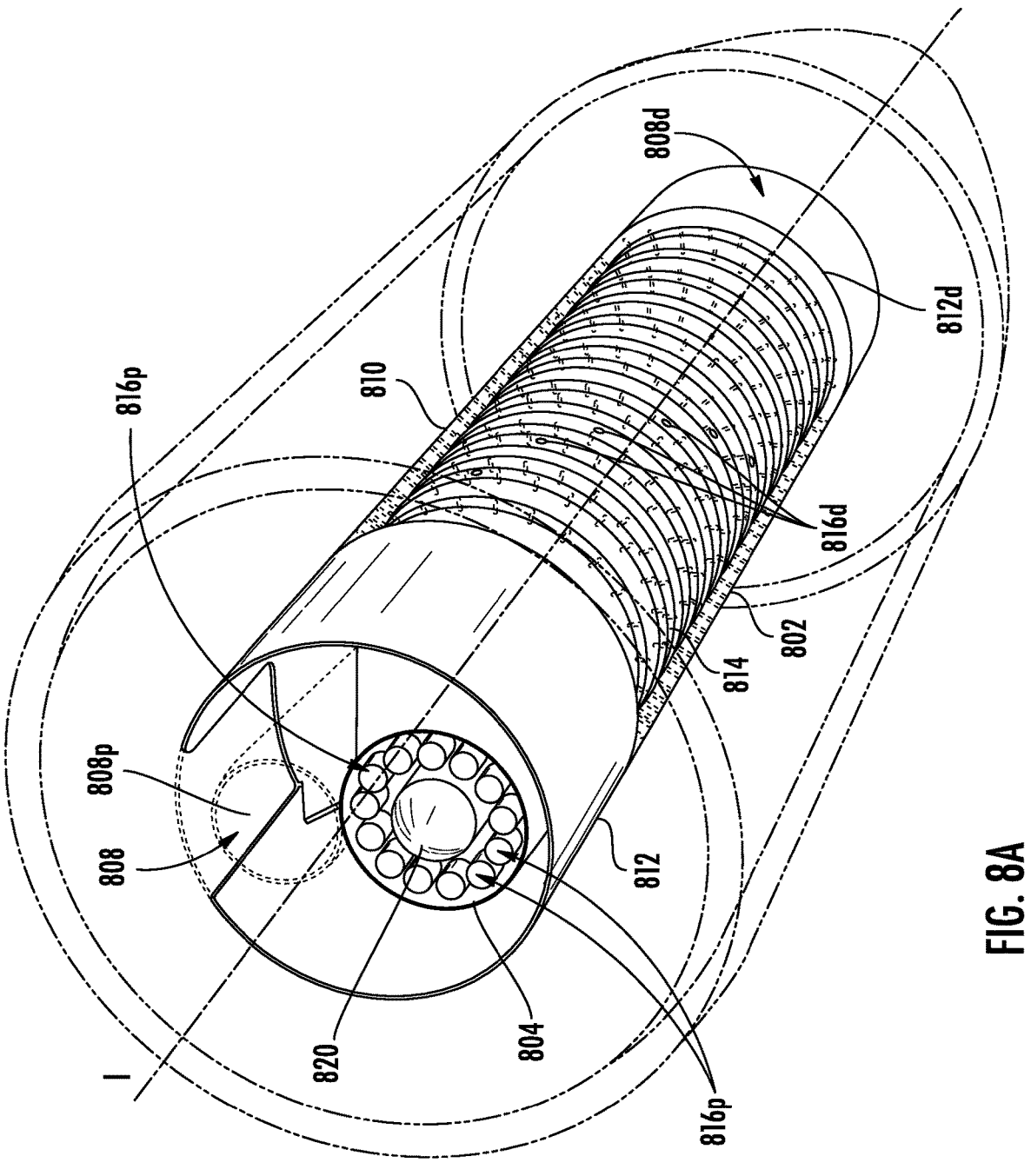
FIGS. 8A and 8B illustrate partial cross-sectional views of a fluid distribution device in accordance with an embodiment of the present disclosure.
Figure 8B:
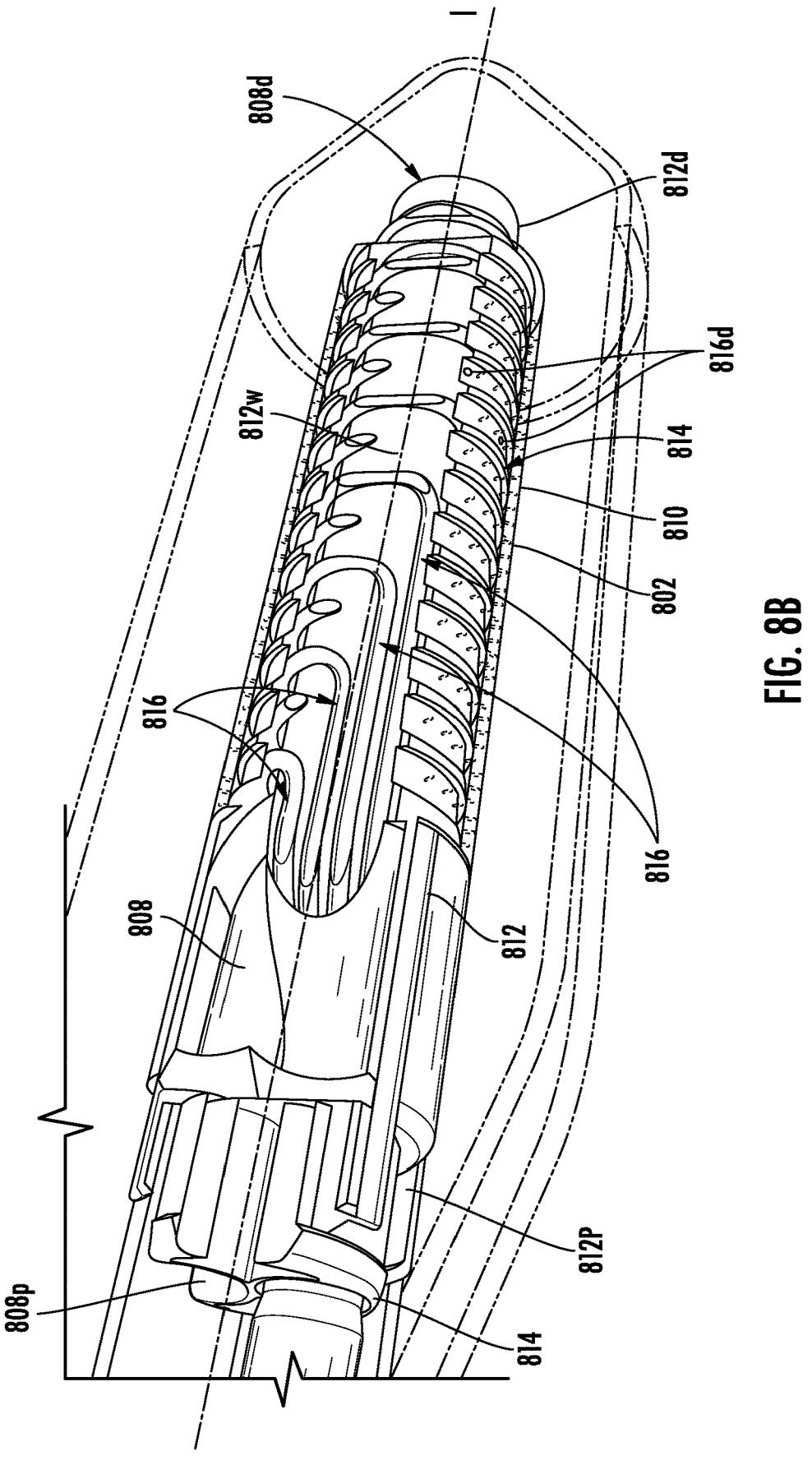

Referring to FIGS. 8A and 8B, an embodiment of a fluid distribution device according to the present disclosure is illustrated, which includes a body 812 having a proximal end 812p, a distal end 812d, and a wall 812w having a width extending therebetween along a longitudinal axis L of the body 812. An inlet 804 extends through the proximal end 812p of the body 812 and is configured to accept a distal end of a delivery catheter. The body 812 includes raised elements 814 disposed on the wall 812w that extend radially outward from the longitudinal axis L (e.g., ribs). The body 812 includes channels 816 that extend from channel inlets 816p in the inlet 804 of the body 812, and each extend independently to a channel aperture 816d in the wall 812w. Each channel 816 extends to a channel aperture 816d between adjacent raised elements 814. Each space between adjacent raised elements 814 has only one channel aperture 816d, but each space may have additional channel apertures 816d to meet flow needs of a procedure. The channels 816 are in fluid communication with the inlet 804 and the space between adjacent raised elements 814 via the channel aperture 816d. The partial cross-sectional views of FIGS. 8A and 8B illustrate portions of the channels 816 extending throughout the body 812. The channels 816 are configured to distribute a flow of fluid from the channel inlets 816p, through the channels 816 along the body 812, out of the channel apertures 816d, into the space between adjacent raised elements 814 and may be used to inject fluid circumferentially about an exterior of the wall 812w, and finally out of the spray apertures 810. The diameter of the channel apertures 816d is larger than the diameter of each spray aperture 810 such that a fluid may flow generally about the circumference of the wall 812w in the spaces between adjacent raised elements 814 before flowing through the spray apertures 810 due to a reduction in diameter in the flow path of the fluid. The diameters of channel apertures 816d may be varied among each other such that, e.g., a distribution of fluid is substantially uniformly distributed among the spaces and out of the apertures 810

Still referring to FIGS. 8A and 8B, a lumen 808 extends through the body 812 substantially in a direction along the longitudinal axis L from a proximal opening 808p at the proximal end of the body 812 to a distal opening 808d at the distal end 812d of the body 812. The lumen 808 is configured to accept a medical instrument therethrough. An elongate tubular member 802 surrounds the body 812 that has spray apertures 810. The spray apertures 810 are arranged about the circumference of the elongate tubular member 802 in rows such that the spray apertures 810 are disposed between adjacent raised elements 814. However, in various embodiments, the arrangement of apertures 810 and raised elements 814 could be of another arrangement among the channels 816, channel apertures 816d, and spray apertures 810, depending on the desired application and effects. The raised elements 814 are in substantial contact with the elongate tubular member 802. The inlet 804 includes a convex protrusion 820 that is oriented in a substantially proximal direction (i.e., such that an apex of the convex protrusion 820 is oriented in a substantially proximal direction). The channels 816 are arranged about the convex protrusion 820 such that a flow of fluid into the inlet 804 may contact the convex protrusion 820 and the fluid may be directed radially away from the apex of the convex protrusion 820 and generally toward the channel inlets 816p. The flow may be distributed in a substantially uniform manner into the channels 816.

In various of the above and other embodiments, expanding an expandable member into contact with a body lumen may be done to position a device/system within a patient, for example, at the substantially central point of the body lumen, such that apertures of a device are substantially equidistant from the walls of the body lumen (i.e., centered within the lumen) or positioned as some other predetermined distance or orientation with respect to the body lumen. The expandable member may also expand into contact with the walls of a body lumen to establish patency.

In various embodiments described here or otherwise within the scope of the present disclosure, the one or more apertures along the wall of the body may be spray apertures. The apertures may be substantially perpendicular to the instrument lumen, the wall of the body, or both. The apertures may be a straight lumen through the wall. The apertures may be a frusto-conical shape with a diameter on the interior of the wall larger than a diameter on the exterior of the wall or vice versa. The one or more apertures may be at an angle to the wall, and the angle may be about 15 degrees to about 165 degrees. One or more of the apertures may be angled to the wall (e.g., not perpendicular to the wall) while one or more of the apertures are perpendicular to the wall. The one or more apertures may create a spray pattern about a full circumference of the body, which may be about 360° about the body. The apertures may be circles, semi-circles, slots, rings, channels, and the like.

In various embodiments, different materials may be selected for various parts of a device or assembly. For example, various portions of a catheter body or a device body may be made up of a stainless steel, a cobalt alloy, a platinum alloy, a combination thereof, or the like. A tube may be laser welded to a body at one or both ends. An expandable member may be made up of PET, PEEK, nylon, stainless steel, or nitinol, or a combination thereof, or the like. A coating may be made up of a urethane, a molded thermoplastic, a thermoplastic urethane, a thermosetting urethane, Pebax, or a thermoplastic elastomer, or a combination thereof, or the like. A sheath may be made up of a coil or braid reinforced polymer, or a polymer encapsulated laser cut metallic tube. A sheath may be provided with or without a lubricious liner, such as PTFE, PFA. An exterior of the sheath may include a lubricious additive, such Propell, or Kemamide. Polymers for the sheath may include Pebax, urethane, polyimide, polyamide, a combination thereof, or the like. Insultation may be made up of a PET braid (e.g., for weak thermal connection with discrete point contact), or a PET heat shrink material (e.g., for barrier to fluid ingress), or a combination thereof, or the like. A catheter may be made up of a laminate of laser cut stainless steel tubing, PET heat shrink tubing, coil-reinforced polymer, such as Pebax, or a combination thereof, or the like.

In various embodiments described here or otherwise within the scope of the present disclosure, the cavity portion of the body may be an annulus. The cavity portion may include a plurality of flow channels within the cavity portion that are configured to evenly distribute flow from the inlet, through the cavity portion, and out the one or more channel and spray apertures. These channels may include walls with a transitioning radius that directs flow from the inlet proximally, toward the one or more apertures in a substantially distal direction. The channels may also direct the flow from the inlet about the cavity portion. The channels may assist in distributing flow evenly throughout the cavity such that cryospray from the apertures is applied to the body lumen in a substantially symmetrical coverage pattern and/or volume, or asymmetrical pattern and/or volume, as desired.

In various embodiments described here or otherwise within the scope of the present disclosure, the cavity portion may be within a housing and about the instrument lumen. The housing may have a proximal end with an inlet extending into the proximal end in fluid communication with the cavity portion. The inlet of the housing may be configured to accept a distal end of the catheter that is configured to deliver a cryogen fluid. The housing may have one or more apertures that are in fluid communication with the cavity portion. The one or more apertures of the housing may be oriented radially from the housing.

In various embodiments described here or otherwise within the scope of the present disclosure, the channel apertures and spray apertures may have a range of dimensions and may have a ratio to increase or decrease a flow rate therethrough. The height, width, and distance between the raised elements, dimensions of the inlet, number and orientation of the channels and apertures, thickness of the various walls of the body and/or walls of the inner manifold, and the transitioning zone may all be chosen, altered and/or optimized for a desired application, fluid used, and/or treatment affect. For example, for $LN_2$, apertures may range from about 0.003 inches (0.0762 mm) to about 0.012 inches (0.3048 mm) in diameter, an annular thickness may range from about 0.005 inches (0.127 mm) to about 0.030 inches (0.762 mm), and walls may range from about 0.005 inches (0.127 mm) to about 0.20 inches (0.508 mm).

In various embodiments described here or otherwise within the scope of the present disclosure, the body may have a pear-shaped cross-section. The body may have other cross-sections such as a circular shape, and elliptical shape, a shape that has a substantially uniform border about the inlet and the instrument lumen, and other shapes that may easily translate within a body lumen. The body may have a blunt tip geometry at the distal end. The blunt tip geometry may assist in inserting the device into the body lumen while minimizing trauma to the body lumen. The body may be a laser cut hypotube, a polymer, or another biocompatible material.

In various embodiments described here or otherwise within the scope of the present disclosure, the catheter, instrument, and/or tubular member may be removable from the fluid distribution device. The device may be permanently attached to the catheter, instrument and/or tubular member. Attachment may include bonding, welding, brazing, or the like.

In various embodiments described here or otherwise within the scope of the present disclosure, the inlet may be parallel to the instrument lumen. An instrument within, in fluid communication with, or in proximity to the instrument lumen may be an endoscope, a guidewire, a CDT, and/or the like. The one or more instruments may be adjacent to the catheter. The inlet and/or the instrument lumen may include one or more detents configured to mate with a projection on the catheter to lock the one or more instruments into a position with respect to the inlet, for example, such that there is fixed spacing between spray treatments, if the device is translatable along the instrument. The instrument lumen may include a channel or track that may be used to slide an instrument along the instrument lumens while maintaining the circumferential orientation of the instrument relative to the distribution device. The inlet may have a diameter configured to interface with the catheter such that the catheter and the inlet are in substantial contact with each other. A transitioning zone may be between and in fluid communication with each of the inlet and the cavity portion. The zone may be configured to increase in volume in a distal direction. The transitioning zone may include one or more interior walls configured to distribute a flow of fluid received from the inlet and conveyed substantially toward the cavity portion.

In various embodiments described here or otherwise within the scope of the present disclosure, an insulating annulus may be a substantially sealed vacuum chamber, a low-conductivity fill medium suitable for use in the cryogenic temperature range, or the insulating annulus may be open to an exterior of the device at a proximal and/or distal end.

In various embodiments described here or otherwise within the scope of the present disclosure, the lumen may include an annular barb configured to interface with a tubular member that extends distally from the lumen and is in fluid communication with the lumen. The barb may interface with an inner surface of the tubular member. The barb may be other shapes such as a ring, a dome, an annulus, a carved-out channel, a protrusion, a bump, or the like that may create friction and interface with the tubular member such that the tubular member is substantially held in place. The instrument lumen may extend distally past the body of a device in order to provide an interface for the tubular member to slide onto.

In various embodiments described here or otherwise within the scope of the present disclosure, the expandable member may be a mesh, braid, spring, balloon, or other expandable feature. The expandable member may be porous such that cryospray may not be substantially obstructed from contacting the body lumen. The expandable member may be used to make a body lumen patent and/or to position a device or instrument within the body lumen, as described above.

Embodiments of a method for distributing fluid, such as cryospray, may include a medical professional inserting a device of the present disclosure into a body lumen. The device may include a delivery catheter with a distal end of the delivery catheter within the device. An additional instrument may be received within and extended through the device. The medical professional may treat a substantially annular section or some desired portion of the annular section of the body lumen without the spray being obstructed by the additional instrument. The spray that translates proximally and distally away from the treatment site within the body lumen may be passively or actively
(e.g., by suction) vented to the atmosphere with the addi-
tional instrument.

All of the devices and/or methods disclosed and claimed
herein can be made and executed without undue experimen-
tation in light of the present disclosure. While the devices
and methods of this disclosure have been described in terms
of preferred embodiments, it will be apparent to those of
skill in the art that variations can be applied to the devices
and/or methods and in the steps or in the sequence of steps
of the method described herein without departing from the
spirit and scope of the disclosure. All such similar substitutes
and modifications apparent to those skilled in the art are
deemed to be within the spirit and scope of the disclosure as
defined by the appended claims.

What is claimed is:

1. A system comprising:
    a device comprising:
        a body having a proximal end, a distal end, and a wall
        having a width extending therebetween along a lon-
        gitudinal axis of the body, the body defining a cavity
        portion and an instrument lumen, wherein the cavity
        portion extends within the body from the proximal
        end to the distal end, and wherein the instrument
        lumen extends through the body parallel to the
        longitudinal axis from an opening at the proximal
        end of the body to an opening at the distal end of the
        body, the instrument lumen configured to receive an
        instrument extending therethrough;
        an inlet at the proximal end of the body, the inlet
        extending into and in fluid communication with the
        cavity portion, the inlet configured to accept a distal
        end of a delivery catheter; and one or more apertures along the wall of the body in
    fluid communication with the cavity portion,
    wherein the one or more apertures are configured to
    spray out a fluid delivered from the delivery catheter
    into the cavity portion through the inlet;
an expandable member about the device; and
a coating extending from a distal end of the expandable
    member and partially toward a proximal end of the
    expandable member, the coating configured to substan-
    tially block fluids from advancing distally past the
    coating.

2. The system of claim 1, wherein the inlet comprises an
elongate surface extending at least partially into the cavity
portion.

3. The system of claim 2, wherein the elongate surface
comprises a step-down portion within the cavity portion, the
step-down portion having a diameter that is smaller than a
diameter of the remainder of the elongate surface.

4. The system of claim 1, wherein the cavity portion is an
annulus and the cavity portion extends about and is closed
to the instrument lumen.

5. The system of claim 1, further comprising a plurality of
flow channels within the cavity portion, the flow channels
configured to distribute flow from the inlet, through the
cavity portion, and out the one or more apertures.

6. The system of claim 1, wherein the one or more
apertures comprise a frusto-conical shape spanning the
width of the wall of the body, and wherein a diameter of the
apertures on an interior surface of the wall is larger than a
diameter of the apertures on an exterior surface of the wall.

*    *    *    *    *